United States Patent
Grant et al.

(10) Patent No.: US 8,025,667 B2
(45) Date of Patent: Sep. 27, 2011

(54) APPARATUS FOR MEASURING AN ANGLE OF A GUIDE WIRE RELATIVE TO A BONE

(75) Inventors: Stuart R. Grant, Warsaw, IN (US); Anthony J. Metzinger, Winona Lake, IN (US); David A. Hawkes, Winona Lake, IN (US); Andrew H. Berthusen, Leesburg, IN (US)

(73) Assignee: DePuy Products, Inc., Warsaw, IN (US)

( * ) Notice: Subject to any disclaimer, the term of this patent is extended or adjusted under 35 U.S.C. 154(b) by 119 days.

(21) Appl. No.: 11/904,399

(22) Filed: Sep. 27, 2007

(65) Prior Publication Data

US 2009/0088768 A1    Apr. 2, 2009

(51) Int. Cl.
*A61B 17/60* (2006.01)
*A61B 17/58* (2006.01)

(52) U.S. Cl. .................. 606/102; 606/86 R; 606/96
(58) Field of Classification Search ........... 606/86 R, 606/96, 102; 33/424, 426, 1 N
See application file for complete search history.

(56) References Cited

U.S. PATENT DOCUMENTS

| | | | | |
|---|---|---|---|---|
| 1,677,396 A | * | 7/1928 | Mickel | 33/424 |
| 1,699,619 A | * | 1/1929 | Muench | 33/476 |
| 2,526,959 A | | 10/1950 | Lorenzo | |
| 2,666,430 A | * | 1/1954 | Gispert | 606/96 |
| 2,697,433 A | * | 12/1954 | Zehnder | 606/96 |
| 3,426,434 A | * | 2/1969 | Zarling | 33/424 |
| 3,554,193 A | | 1/1971 | Konstantinou et al. | |
| 4,221,055 A | * | 9/1980 | Delgado | 33/418 |
| 4,421,112 A | * | 12/1983 | Mains et al. | 606/88 |
| 4,438,762 A | | 3/1984 | Kyle | |
| 4,440,168 A | * | 4/1984 | Warren | 606/102 |
| 4,465,065 A | | 8/1984 | Gotfried | |
| 4,920,958 A | * | 5/1990 | Walt et al. | 606/96 |
| 5,070,623 A | * | 12/1991 | Barnes | 33/807 |
| 5,078,719 A | * | 1/1992 | Schreiber | 606/87 |
| 5,205,045 A | * | 4/1993 | Liu | 33/468 |
| 5,254,119 A | * | 10/1993 | Schreiber | 606/87 |
| 5,324,292 A | | 6/1994 | Meyers | |
| 5,350,383 A | * | 9/1994 | Schmieding et al. | 606/96 |
| 5,449,360 A | * | 9/1995 | Schreiber | 606/87 |
| 5,458,602 A | * | 10/1995 | Goble et al. | 606/96 |
| 5,601,562 A | * | 2/1997 | Wolf et al. | 606/86 R |

(Continued)

FOREIGN PATENT DOCUMENTS

EP    1470792    10/2004

(Continued)

OTHER PUBLICATIONS

DePuy Orthopaedics' brochure entitled "Captured Hip Screw System Surgical Technique"; Published at least as early as Sep. 26, 2007; Nineteen (19) pages.

(Continued)

*Primary Examiner* — Thomas C. Barrett
*Assistant Examiner* — Michael T Schaper

(57) ABSTRACT

A measurement apparatus has a body that includes a reference surface that defines a reference line. The body further includes a first elongate window defining a first measurement line and a first measurement indicia positioned in association with the first elongate window. The first measurement line and the reference line define a first angle having a first magnitude. The first measurement indicia corresponds to the first magnitude.

22 Claims, 23 Drawing Sheets

U.S. PATENT DOCUMENTS

| | | | | |
|---|---|---|---|---|
| 5,643,273 | A * | 7/1997 | Clark | 606/96 |
| D402,217 | S * | 12/1998 | Taylor | D10/65 |
| 5,891,150 | A * | 4/1999 | Chan | 606/96 |
| 5,968,050 | A * | 10/1999 | Torrie | 606/87 |
| 5,983,509 | A * | 11/1999 | Gosselin et al. | 33/1 SD |
| 6,007,535 | A * | 12/1999 | Rayhack et al. | 606/57 |
| 6,120,511 | A * | 9/2000 | Chan | 606/96 |
| 6,342,056 | B1 * | 1/2002 | Mac-Thiong et al. | 606/96 |
| 6,361,506 | B1 * | 3/2002 | Saenger et al. | 600/587 |
| 6,623,488 | B1 * | 9/2003 | Leone, Jr. | 606/102 |
| 6,954,990 | B2 * | 10/2005 | Ellis | 33/471 |
| 7,056,322 | B2 | 6/2006 | Davison et al. | |
| 7,192,431 | B2 * | 3/2007 | Hangody et al. | 606/87 |
| 7,192,432 | B2 * | 3/2007 | Wetzler et al. | 606/96 |
| 2005/0080428 | A1 * | 4/2005 | White | 606/102 |
| 2005/0177171 | A1 * | 8/2005 | Wetzler et al. | 606/96 |
| 2005/0203532 | A1 * | 9/2005 | Ferguson et al. | 606/90 |
| 2005/0216026 | A1 | 9/2005 | Culbert | |
| 2006/0052795 | A1 * | 3/2006 | White | 606/102 |
| 2006/0058810 | A1 * | 3/2006 | Wozencroft et al. | 606/102 |
| 2007/0162011 | A1 | 7/2007 | Leyden et al. | |

FOREIGN PATENT DOCUMENTS

| | | |
|---|---|---|
| WO | 2006029346 | 3/2006 |
| WO | WO 2005/084559 | 9/2006 |
| WO | WO 2005/084560 | 9/2006 |

OTHER PUBLICATIONS wisdomking.com web site: *Plastic 180° Pocket Goniometer—121005;* http://www.wisdomking.com/product55238.html. Downloaded from website on Sep. 9, 2007 (2 pages).

Amazon.com website: *"goniometer"*, http://www.amazon.com/exec/obidos/search-handle-url/index=blended&field-keywords=go... Downloaded from website on Sep. 9, 2007 (4 pages).

Patent Cooperation Treaty, International Search Report in a corresponding PCT application (i.e. PCT/US2008/076955), dated Feb. 6, 2009, 4 pages.

\* cited by examiner

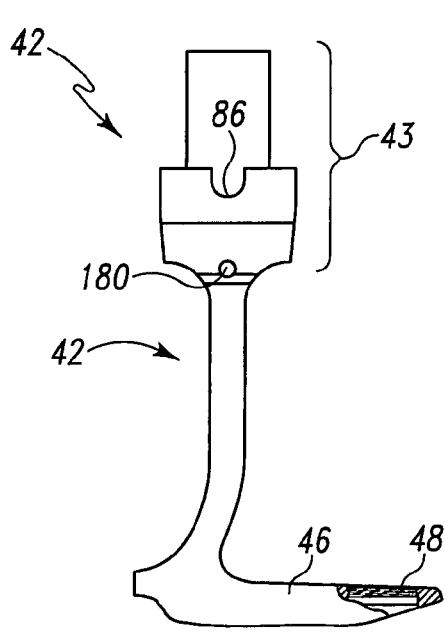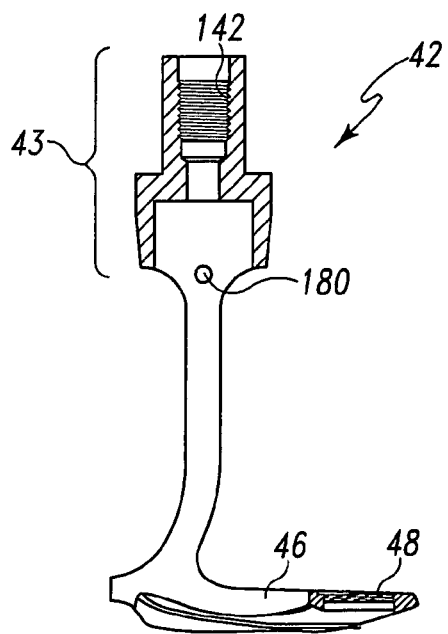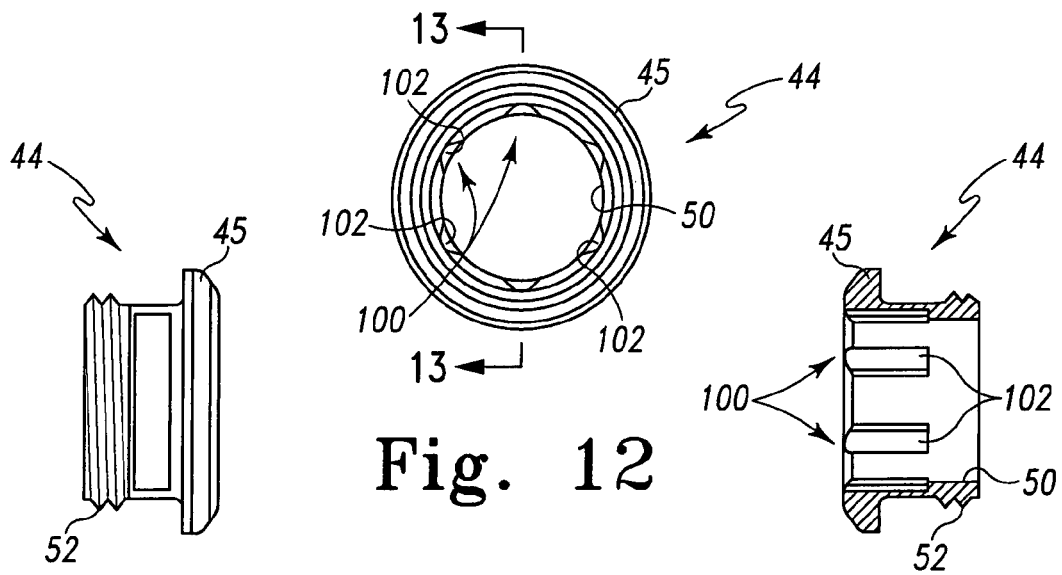

APPARATUS FOR MEASURING AN ANGLE OF A GUIDE WIRE RELATIVE TO A BONE

CROSS REFERENCE TO RELATED APPLICATIONS

Cross reference is made to copending (i) U.S. patent application Ser. No. 11/904,414, entitled "Plate Holder Assembly having Movable Guide Component" by Richard Kyle, Jeffrey Waffensmith, Matthew Leyden, Tim Bachman, Matthew Wallace, and Marc Ruhling, (ii) U.S. patent application Ser. No. 11/904,504, entitled "Plate Holder Assembly having Bone Plate Seating Confirmation Arrangement" by Matthew Leyden, Jeffrey Waffensmith, Tim Bachman, Matthew Wallace, Marc Ruhling, Anthony J. Metzinger, and Charles Christie, (iii) U.S. patent application Ser. No. 11/904,476, entitled "Plate Holder and Bone Plate Arrangement" by Matthew Leyden, Jeffrey Waffensmith, Matthew Wallace, and Marc Ruhling, and (iv) U.S. patent application Ser. No. 11/904,520, entitled "Guide Assembly for Use in a Medical Procedure" by Matthew Leyden, Aaron Bisek, David A. Hawkes, Marc Ruhling, Jeffrey Waffensmith, and Matthew Wallace, which are assigned to the same assignee as the present invention, and which are filed concurrently herewith. The disclosures of the four above-identified patent applications are herein totally incorporated by reference in their entirety.

BACKGROUND

The present disclosure relates generally to measuring devices, and more particularly, to apparatus for measuring an angle of a guide wire relative to a bone.

A procedure regularly performed by orthopedic surgeons is the reduction of a hip fracture caused by trauma. The site of this type of fracture typically exists at the proximal portion of the femur below the head. In order to reduce a fracture of this type, an elongated lag screw is threadingly advanced over a guide wire into the shaft, neck, and head of the femur, and secured to a bone plate. Cortical screws are used to secure the bone plate to the femur distal to the fracture site. Tightening of the lag screw compresses the bone fragments together and facilitates healing of the femur. Many devices have been designed for this type of reduction including the devices disclosed in U.S. Pat. Nos. 4,438,762, 3,554,193, and 2,526,959, the disclosures of which are incorporated herein by reference in their entirety.

One step in the above-described procedure is to measure the angle of the guide wire relative to the femur to obtain an anteversion angle of the femur. In response to this measurement, an appropriately configured barrel (or fastener guide) may be selected for use in the lag screw assembly that is to be implanted in the femur. In particular, a barrel having a configuration that corresponds to the anteversion angle of the femur is selected, and thereafter joined with a lag screw to form a lag screw assembly that is then implanted over the guide wire in the femur.

Measurement of the guide wire relative to the femur may be made by a surgeon while the guide wire is located within the body of a patient, and in particular, positioned in the shaft, neck, and head of the femur of the patient. Alternatively, the measurement may be made while the guide wire is not located in the body of the patient, but rather is merely positioned on top of the patient's body in a position over the shaft, neck, and head of the femur.

One measurement apparatus that has been used to measure the angle of a guide wire relative to a femur to obtain an anteversion angle of the femur is a goniometer. Another measurement apparatus that has been used to measure such angle is a protractor.

It would be advantageous to design a measuring apparatus that facilitates precise measurement of the angle of a guide wire relative to a femur. It would be beneficial if such measuring apparatus was relatively easy to use. It would be additionally advantageous if such measuring apparatus could be used in association with an X-ray procedure to obtain highly accurate measurements. It would also be beneficial if such measuring device would facilitate advancement of a guide wire into the femur at a predetermined angle.

What is needed therefore is an apparatus for measuring an angle of a guide wire relative to a bone such as a femur that facilitates precise measurement. What is also needed is such a measuring apparatus that is relatively easy to use. What is further needed is an apparatus for measuring an angle of a guide wire relative to a bone that could be used in association with an X-ray procedure to obtain highly accurate measurements. What is additionally needed is an apparatus for measuring an angle of a guide wire relative to a femur that facilitates advancement of a guide wire into the femur at a predetermined angle.

SUMMARY

In accordance with one embodiment of the disclosure, there is provided a measurement apparatus has a body that includes a reference surface that defines a reference line. The body further includes a first elongate window defining a first measurement line and a first measurement indicia positioned in association with the first elongate window. The first measurement line and the reference line define a first angle having a first magnitude. The first measurement indicia corresponds to the first magnitude.

Pursuant to another embodiment of the disclosure, there is provided a measurement apparatus that has a body that includes a reference surface that defines a reference line. The body further includes a plurality of windows that define a first measurement line and a first measurement indicia positioned in association with the first plurality of windows. The first measurement line and the reference line define a first angle having a first magnitude. The first measurement indicia corresponds to the first magnitude.

In accordance with yet another embodiment of the disclosure, there is provided a measurement apparatus. The measurement apparatus includes a body including (i) a reference surface that defines a reference line, (ii) a first measurement line, and (iii) a first measurement indicia positioned in association with the first measurement line, wherein the first measurement line and the reference line define a first angle having a first magnitude, and further wherein the first measurement indicia corresponds to the first magnitude. The measurement apparatus further includes a guide wire catch projecting from the body, wherein (i) the body defines a plane P, (ii) the guide wire catch includes a first catch portion and a second catch portion, (iii) the first catch portion is positioned on a first side of the plane P, and (iv) the second catch portion is positioned on a second side of the plane P.

BRIEF DESCRIPTION OF THE DRAWINGS

FIG. 9 is a side elevational view of the plate holder of the instrument assembly of FIG. 5;

FIG. 10 is a cross sectional view of the plate holder of the instrument assembly of FIG. 5;

FIG. 11 is a side elevational view of the coupling component of the instrument assembly of FIG. 5;

FIG. 12 is a top elevational view of the coupling component of the instrument assembly of FIG. 5;

FIG. 13 is a cross sectional view of the coupling component taken along the line 13-13 of FIG. 12;

DESCRIPTION OF THE PREFERRED EMBODIMENTS

Figure 1:
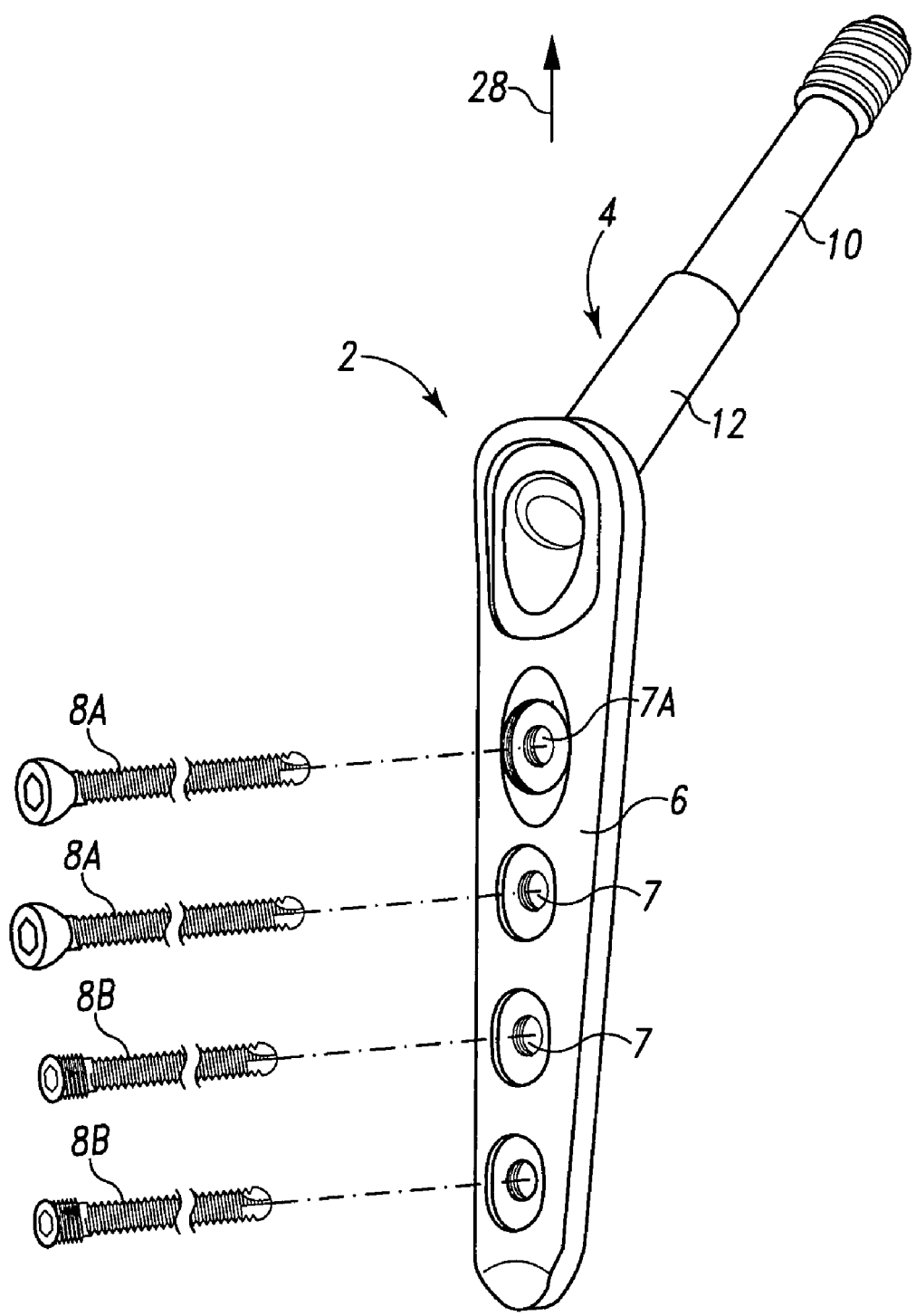
FIG. 1 is a perspective view of an implant assembly which is implanted in a minimally invasive manner according to the present disclosure.
Figure 2A:
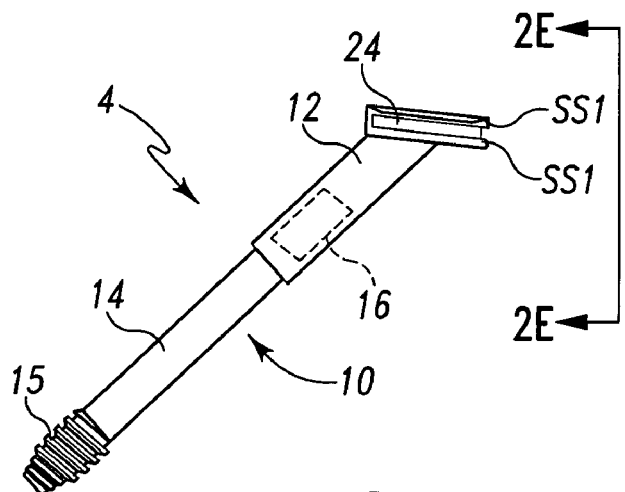
FIG. 2A is a side elevational view of the lag screw assembly of the implant assembly of FIG. 1.
Figure 2B:
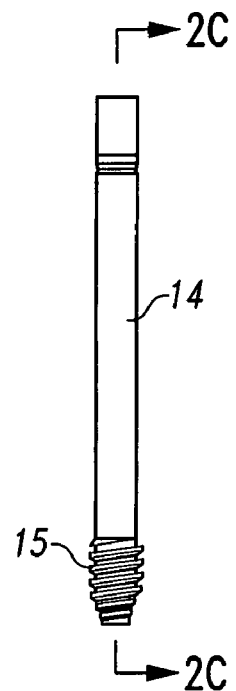
FIG. 2B is a side elevational view of the lag screw component of the lag screw assembly of FIG. 2A.
Figure 2D:
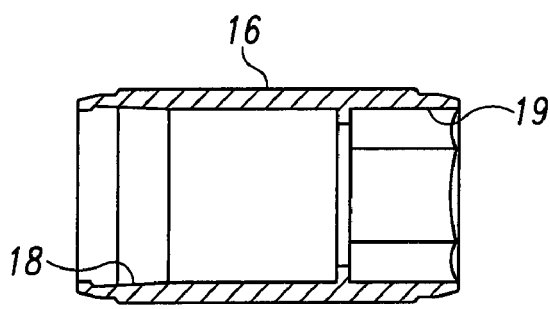
FIG. 2D is a cross sectional view of the sleeve of the lag screw assembly of FIG. 2A.
Figure 2E:
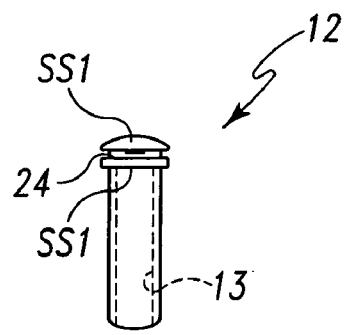
FIG. 2E is a side elevational view of the fastener guide taken along the line 2E-2E of FIG. 2A.
Figure 2C:
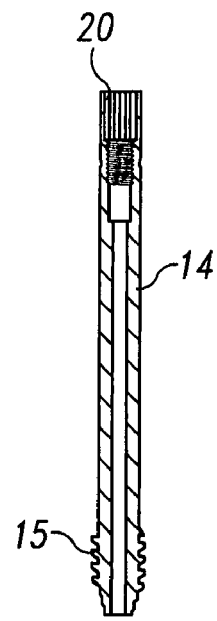
FIG. 2C is a cross sectional view of the lag screw component taken along the line 2C-2C of FIG. 2B.

While the measurement apparatus described herein is susceptible to various modifications and alternative forms, specific embodiments thereof have been shown by way of example in the drawings and will herein be described in detail. It should be understood, however, that there is no intent to limit the measurement apparatus to the particular forms disclosed, but on the contrary, the intention is to cover all modifications, equivalents, and alternatives falling within the spirit and scope of the invention as defined by the appended claims.

Instrumentation and Implant Components

Described below are instrumentation and implant components that facilitate reduction of a hip fracture in a minimally invasive manner. As shown in FIGS. 1, 2A-2E, and 3A-3D, the implant components include an implant assembly 2 that includes a lag screw assembly 4, a bone plate 6, and a plurality of bone screws 8A, 8B. The bone screws 8A include two non-locking cortical bone screws, while the bone screws 8B include two locking cortical bone screws. Alternatively, other combinations of locking screws 8A and non-locking screws 8B may be used with the bone plate 6. Further, instead of using a combination of locking and non-locking screws, all locking screws 8B may used with the bone plate 6, or alternatively all non-locking screws 8A may be used with the bone plate 6.

Figure 3A:
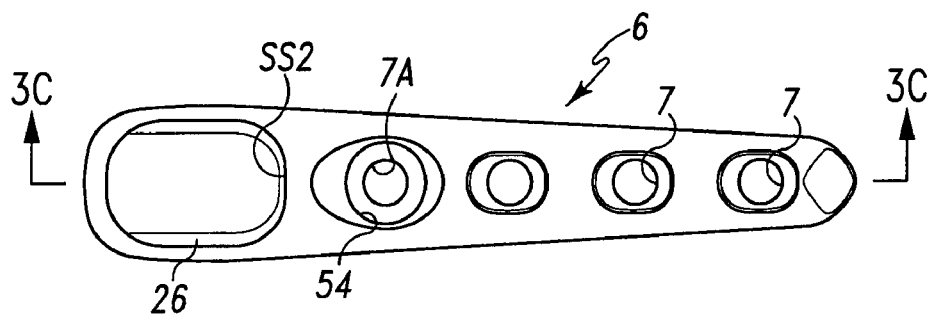
FIG. 3A is a top elevational view of the bone plate of the implant assembly of FIG. 1.
Figure 3B:
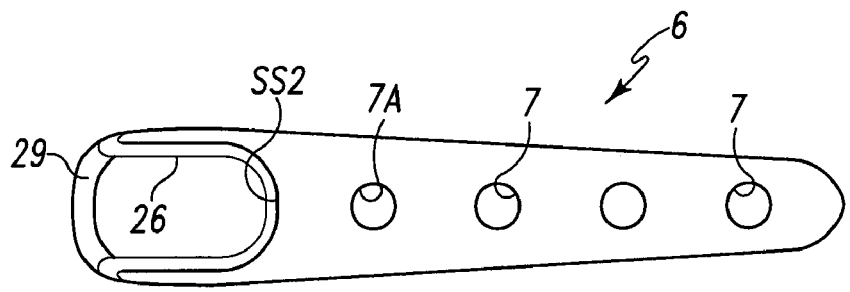
FIG. 3B is a bottom elevational view of the bone plate of the implant assembly of FIG. 1.
Figure 3C:
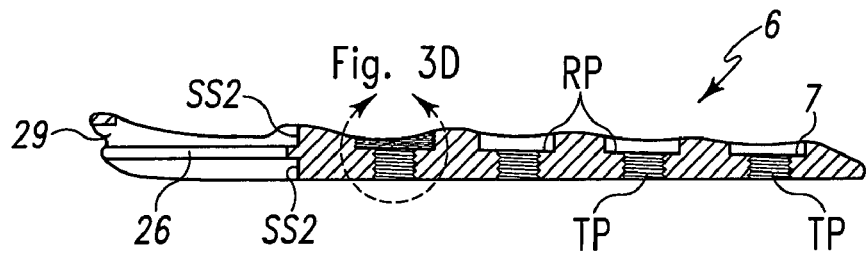
FIG. 3C is a cross sectional view of the bone plate taken along the line 3C-3C of FIG. 3A.
Figure 3D:
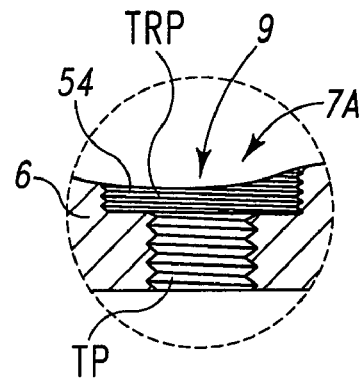
FIG. 3D is an enlarged, fragmentary, cross sectional view of the bone plate showing the portion of FIG. 3C that is encircled and identified as FIG. 3D.

The bone plate 6 has defined therein a plurality of fastener openings 7, 7A configured to receive the bone screws 8A, 8B. Each of the fastener openings 7 include a recess portion RP and a threaded portion TP that are aligned with each other as shown in FIG. 3C. The fastener opening 7A includes a threaded recess portion TRP and a threaded portion TP that are aligned with each other as shown in FIG. 3D. The threaded recess portion TRP defines a set of internal threads 54. The structure of the bone plate 6 that defines the threaded recess portion TRP creates a coupling component 9.

The lag screw assembly 4 includes a lag screw 10 and a fastener guide or barrel 12. The fastener guide 12 defines a passage 13 in which the lag screw 10 is partially positioned. The lag screw 10 includes a lag screw component 14 and a sleeve 16 that are rotatably attached together. The lag screw component 14 has defined therein a plurality of threads 15. The sleeve 16 is configured to slide axially within the passage 13 of the fastener guide 12, but is prevented from being able to rotate in relation to the fastener guide 12 by mating structure (not shown) of the sleeve 16 and fastener guide 12. The sleeve 16 has defined therein a passage 18 that defines a hexagonal shaped recess 19. The lag screw component 14 is freely rotatable in relation to the sleeve 16. However, when a keying mechanism (not shown) is positioned within the recess 19 of the sleeve 16 and a hexagonal-shaped recess 20 of the lag screw component 14, the sleeve 16 and the lag screw component 14 are rotationally or angularly locked together. In other words, rotation of the sleeve 16 causes rotation of the lag screw component 14. Thus, when the keying mechanism is positioned within the recess 19 and the recess 20, the lag screw component 14 is rotationally or angularly locked in relation to the fastener guide 12 since the sleeve 16 is prevented rotating in relation to the fastener guide 12 as discussed above. However, the lag screw component 14 is able to slide axially in relation to the passage 13 of the fastener guide 12.

Alternatively, the sleeve 16 may be permanently fixed in relation to the lag screw component 14 so that, after assembly of these components, rotation of the sleeve 16 causes rotation of the lag screw component 14. An alternative lag screw assembly that may be utilized in the lag screw assembly 4 is the lag screw assembly disclosed in U.S. Patent Application Publication No. US2007/0162011, having a U.S. application Ser. No. 11/303,833, the disclosure of which is herein incorporated by reference in its entirety.

The bone plate 6 cooperates with the lag screw assembly 4 to assume the configuration shown in FIG. 1. In particular, the fastener guide 12 defines a channel 24. The channel 24 is preferably U-shaped. The bone plate 6 defines an access opening 29 through which the fastener guide 12 may advance. The bone plate 6 includes a projection 26. The projection 26 is preferably U-shaped. The projection 26 of the bone plate 6 is configured to be received within the channel 24 of fastener guide 12. In order to mate the bone plate 6 with the lag screw assembly 4, the bone plate 6 is advanced in the direction indicated by arrow 28 (see FIG. 1) so that the fastener guide 12 passes through the access opening 29 of the bone plate whereby the projection 26 of the bone plate is received within the channel 24 of the fastener guide. Continued advancement of the bone plate 6 in relation to the fastener guide 12 in the direction of arrow 28 results in a seating surface SS1 of the fastener guide 12 contacting a seating surface SS2 of the bone plate 6. When seating surface SS1 is positioned in contact with the seating surface SS2, the bone plate 6 and the fastener guide 12 are in an assembled state.

Figure 4:
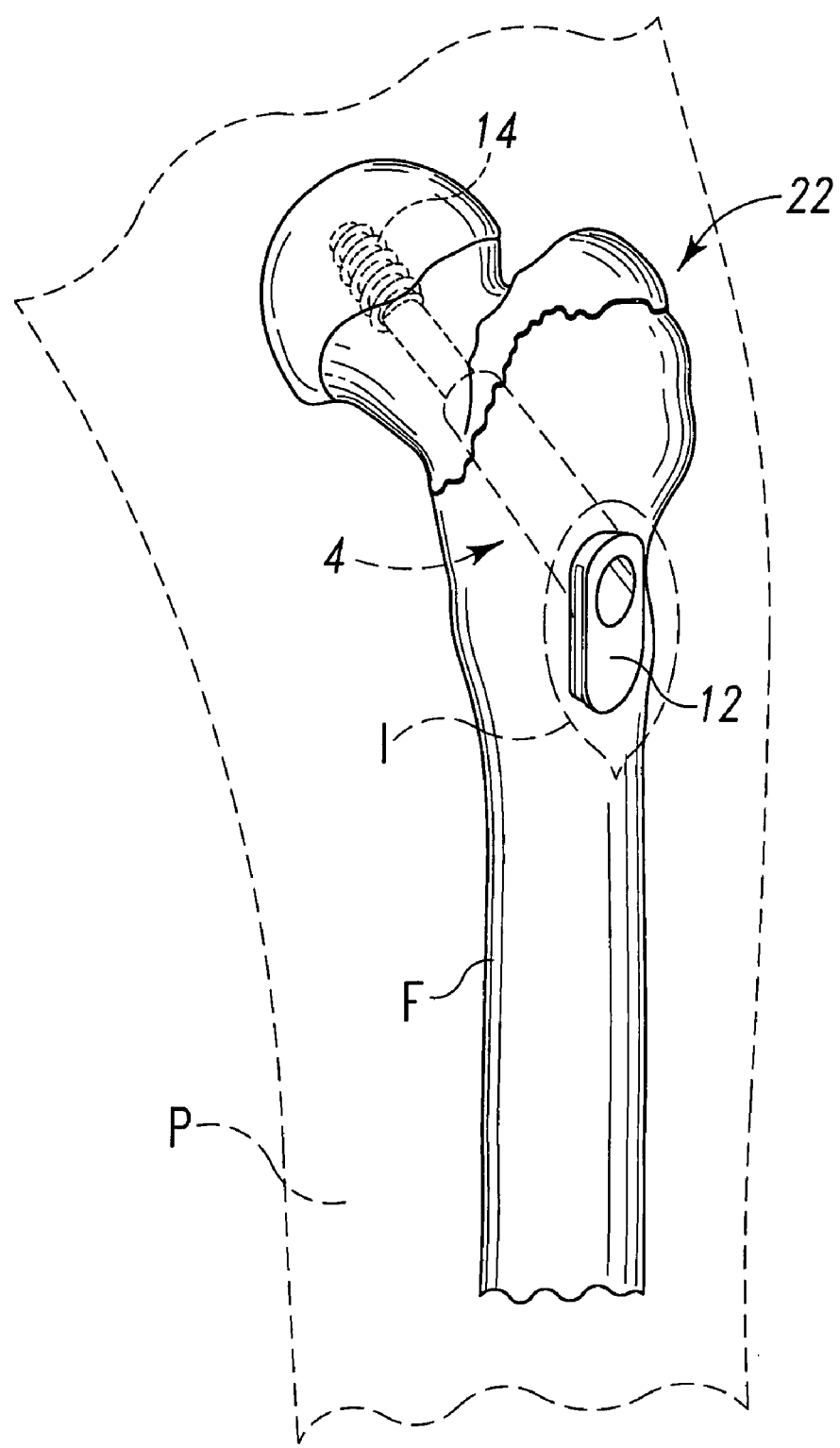
FIG. 4 is a perspective view of the lag screw assembly of FIG. 2A implanted in a femur of a patient according to the present disclosure, with the lag screw assembly being partially visually exposed through an incision in a patient.

At a particular stage during a hip fracture reduction procedure, the lag screw assembly 4 is secured within a femoral head, neck, and shaft of a femur F of a patient P as shown in FIG. 4. The lag screw assembly 4 is partially visually exposed through an incision I in the patient P as shown in FIG. 4. The femur F has a fracture 22 defined therein as shown in FIG. 4.

Figure 36:
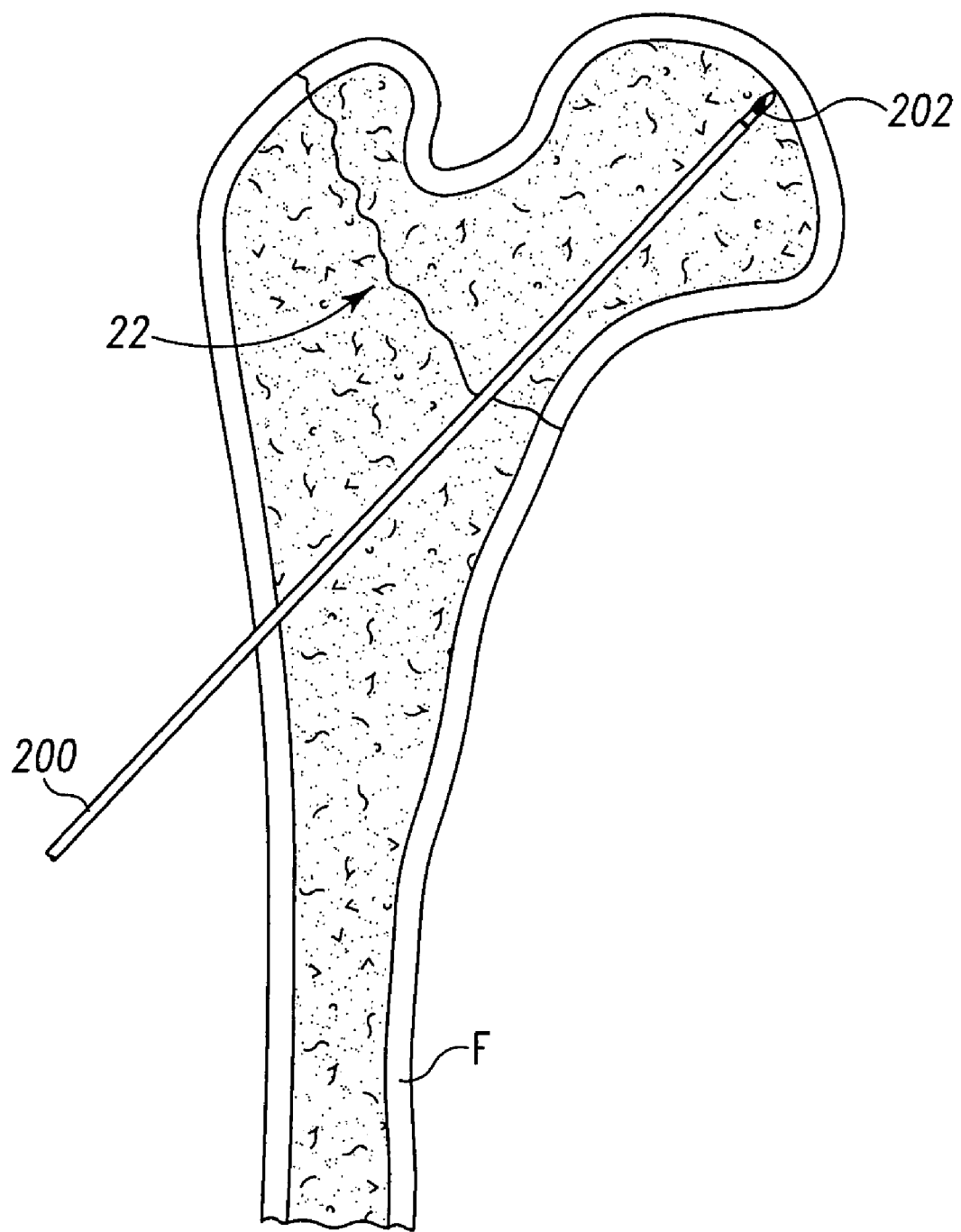
FIG. 36 is a fragmentary side elevational view of the guide wire of FIG. 37 positioned in the femur of FIG. 4, with the femur shown in cross section.

In order to facilitate placement of the lag screw assembly 4 as shown in FIG. 4, a surgeon advances a guide wire 200 into the shaft, neck, and head of the femur F through the incision I to the position shown in FIG. 36. Note the guide wire 200 is advanced until threads 202 of the guide wire 200 are secured to subchondral bone in the center of the head of the femur F in both anterior-posterior and lateral views.

Figure 37:
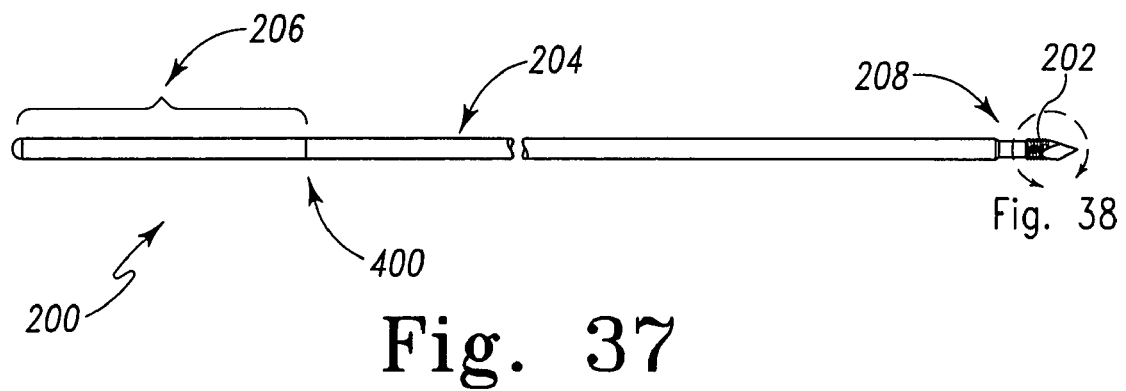
FIG. 37 is a side elevational view of a guide wire which is used to implant the lag screw assembly of FIG. 2A in a minimally invasive manner according to the present disclosure.
Figure 38:
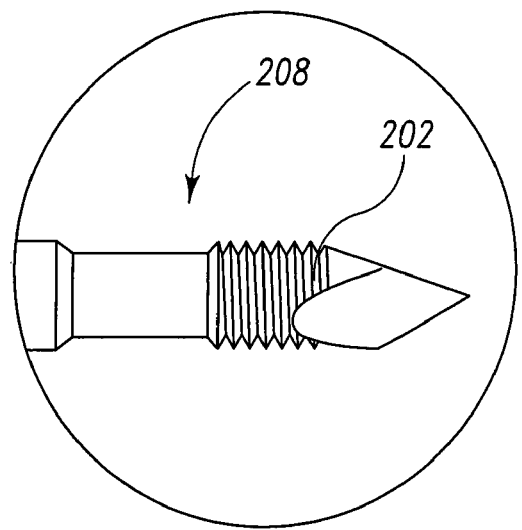
FIG. 38 is an enlarged, side elevational view of the portion of the guide wire of FIG. 37 that is encircled and identified as FIG. 38.

The guide wire 200, which is preferably a 3.2 mm guide wire, is shown in more detail in FIGS. 37-38. The guide wire 200 includes an elongate body 204 having a proximal portion 206 and a distal portion 208. The distal portion 208 includes threads 202 as shown in FIGS. 37-38. The proximal portion 206 is preferably colored black, while the rest of the guide wire 200 is preferably colored metallic gray or silver.

After the guide wire 200 is advanced into the femur F to the position shown in FIG. 36, a fastener cavity (not shown) is created in the femur F with a cannulated drill (not shown) being advanced over the guide wire 200. Thereafter, a cannulated tap (not shown) may be advanced over the guide wire 200 and into the fastener cavity to create female (internal) screw threads (not shown) in the internal walls defining the fastener cavity to prepare the fastener cavity for receipt of the lag screw assembly 4.

In order to facilitate selection of a lag screw assembly 4 having an appropriately configured barrel 12, the angle of the guide wire 200 relative to the femur F must be determined. To this end, a measurement apparatus 210 is utilized to determine such angle. The measurement apparatus 210 is shown in detail in FIGS. 39-42.

Figure 39:
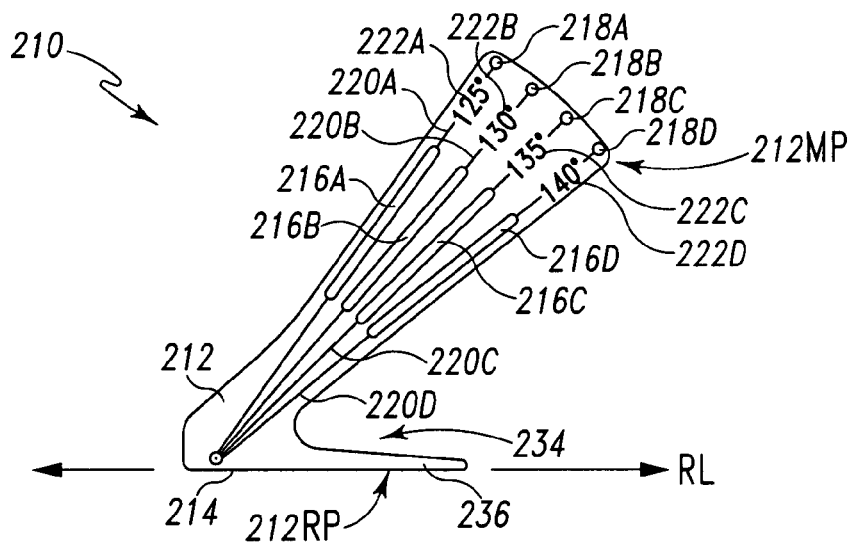
FIG. 39 is a side elevational view of a measurement apparatus which is used to measure the angle of a guide wire in relation a femur according to the present disclosure.
Figure 40:
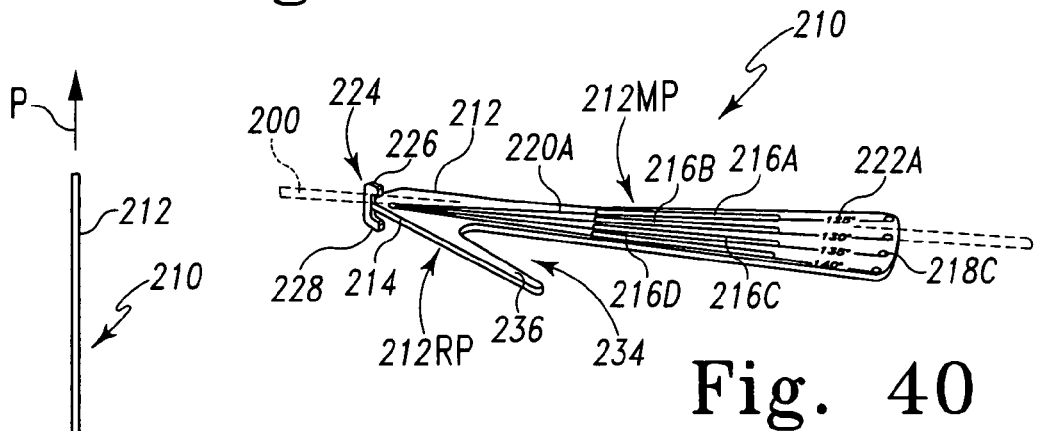
FIG. 40 is a perspective view of the measurement apparatus of FIG. 39.

The measurement apparatus 210 is made from a radio opaque material, which is preferably stainless steel. The measurement apparatus 210 includes a body 212. The body 212 includes a reference surface 214 that defines a reference line RL. The body 212 further includes a number of elongate windows 216A, 216B, 216C, and 216D. The windows 216A, 216B, 216C, and 216D are spaced apart from each other as shown in FIGS. 39-40. As shown in FIG. 39, the elongate window 216A is configured to define a measurement line 220A, while the elongate window 216B is configured to define a measurement line 220B. Further, as shown in FIG. 39, the elongate window 216C is configured to define a measurement line 220C, while the elongate window 216D is configured to define a measurement line 220D.

The body 212 further includes a measurement indicia 222A that is positioned in association with the elongate window 216A as shown in FIG. 39. In particular, the measurement indicia 222A is positioned in relation the elongate window 216A so that a user of the measurement apparatus 210 is informed that the measurement line 220A represents a magnitude of an angle defined by the measurement line 220A and the reference line RL.

The body 212 further includes measurement indicia 222B, 222C, and 222D. The measurement indicia 222B is positioned in association with the elongate window 216B, and the measurement indicia 222C is positioned in association with the elongate window 216C, and the measurement indicia 222D is positioned in association with the elongate window 216D. So positioned, the measurement indicia 222B is located in relation the elongate window 216B so that a user of the measurement apparatus 210 is informed that the measurement line 220B represents a magnitude of an angle defined by the measurement line 220B and the reference line RL. Similarly, the measurement indicia 222C is located in relation the elongate window 216C so that a user of the measurement apparatus 210 is informed that the measurement line 220C represents a magnitude of an angle defined by the measurement line 220C and the reference line RL. And the measurement indicia 222D is located in relation the elongate window 216D so that a user of the measurement apparatus 210 is informed that the measurement line 220D represents a magnitude of an angle defined by the measurement line 220D and the reference line RL. The measurement indicia 222A is "125°", while the measurement indicia 222B is "130°". Further, the measurement indicia 222C is "135°", while the measurement indicia 222D is "140°".

As further shown in FIGS. 39-40, the measurement line 220A and the reference line RL define an angle having a magnitude of 125°, while the measurement line 220B and the reference line RL define an angle having a magnitude of 130°. Also, the measurement line 220C and the reference line RL define an angle having a magnitude of 135°, while the measurement line 220D and the reference line RL define an angle having a magnitude of 140°. Thus, the measurement indicia 222A, 222B, 222C, and 222D corresponds to and informs a user of the actual magnitude of the angles that are defined by the measurement lines 220A, 220B, 220C, and 220D and the reference RL, respectively.

The body 212 further includes a number of other windows 218A, 218B, 218C, and 218D. The windows 218A, 218B, 218C, and 218D are spaced apart from each other as shown in FIGS. 39-40. In addition, the windows 218A, 218B, 218C, and 218D are spaced apart from the windows 216A, 216B, 216C, and 216D as shown in FIGS. 39-40. It should be appreciated that the window 218A and the window 216A are arranged to also define the measurement line 220A, while the window 218B and the window 216B are arranged to also define the measurement line 220B. Further, as shown in FIG. 39, the window 218C and the window 216C are arranged to also define the measurement line 220C, while the window 218D and the window 216D are arranged to also define the measurement line 220D.

Figure 42:
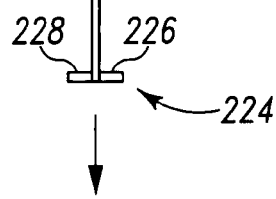
FIG. 42 is a front elevational view of the measurement apparatus of FIG. 39.
Figure 41:
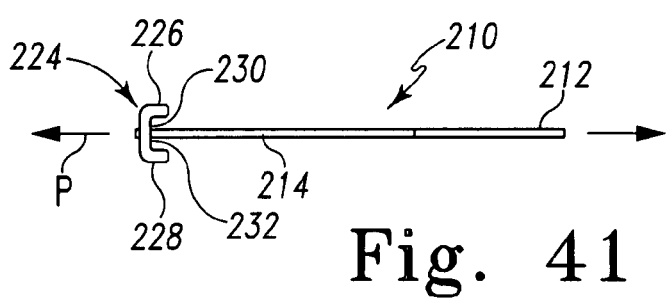
FIG. 41 is a bottom elevational view of the measurement apparatus of FIG. 39.

The body 212 of the measurement apparatus 210 defines a plane P as shown in FIGS. 41-42. The measurement apparatus 210 includes a catch 224 configured to receive and support the guide wire 200 as shown in FIG. 40. The catch 224 includes a catch portion 226 and a catch portion 228. The catch portion 226 is located on one side of the plane P, while the catch portion 228 is located on another side of the plane P as shown in FIGS. 41-42. As shown in FIGS. 40-41, the catch portion 226 defines a hook that is configured to receive and support the guide wire 200. Similarly, the catch portion 228 defines a hook that is configured to receive and support the guide wire 200. Thus, the measurement apparatus 210 is configured to be used with the guide wire 200 positioned on either the left side of plane P, or the right side of the plane P (as the plane P is viewed in FIG. 42).

The hook defined by the catch portion 226 includes a contact surface 230, while the hook defined by the catch portion 228 includes a contact surface 232. As shown in FIG. 40, the guide wire 200 (shown in phantom) is positioned during use on the side of the plane P such that the guide wire 200 is positioned in contact with both the contact surface 230 and the body 212. Alternatively, the guide wire 200 may be positioned during use on the other side of the plane P such that the guide wire 200 is positioned in contact with both the contact surface 232 and the body 212.

Figure 43:
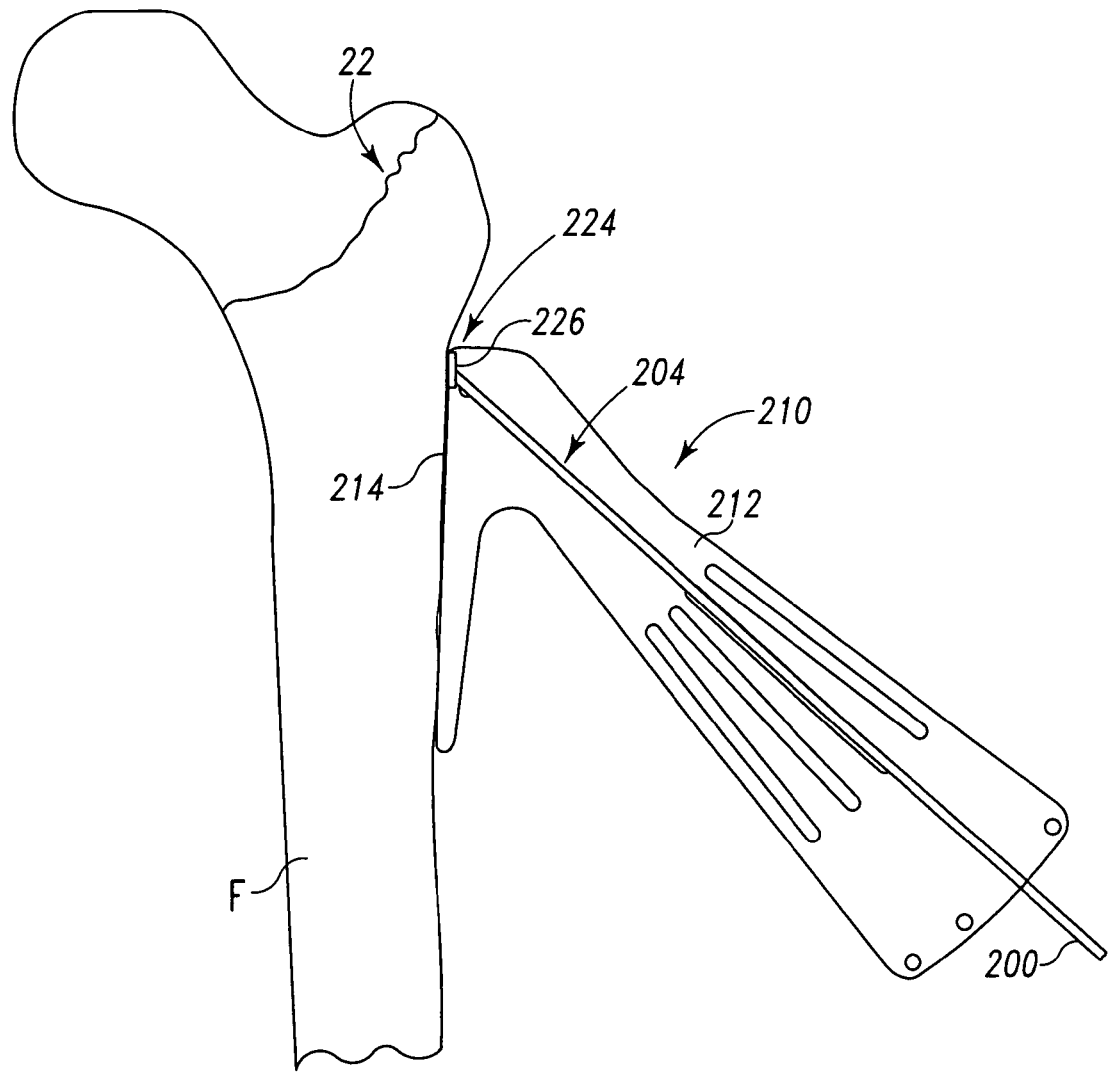
FIG. 43 is a side elevational view of the measurement apparatus of FIG. 39 being used to measure the angle of the guide wire of FIG. 37 with respect to the femur after the guide wire has been advanced into the femur.

The body 212 includes a measurement portion 212MP and a reference portion 212RP. As shown in FIGS. 39-40, the measurement portion 212MP has the windows 216A, 216B, 216C, 216D, 218A, 218B, 218C, and 218D defined therein. As also shown in FIGS. 39-40, the reference portion 212RP includes the reference surface 214. A gap 234 is defined between the measurement portion 212MP and the reference portion 212RP as shown in FIGS. 39-40. The reference portion 212RP includes a finger 236 that extends away from the measurement portion 212MP. The finger 236 of the measurement apparatus 210 is advantageously configured so that, during use of the measurement apparatus 210 by a surgeon, the finger 236 is conveniently advanced through the incision I (see FIG. 4) in the body of the patient P, and thereafter the surgeon may manipulate the measurement apparatus so as to position the reference surface 214 against the femur F as shown in FIG. 43.

Figure 5:
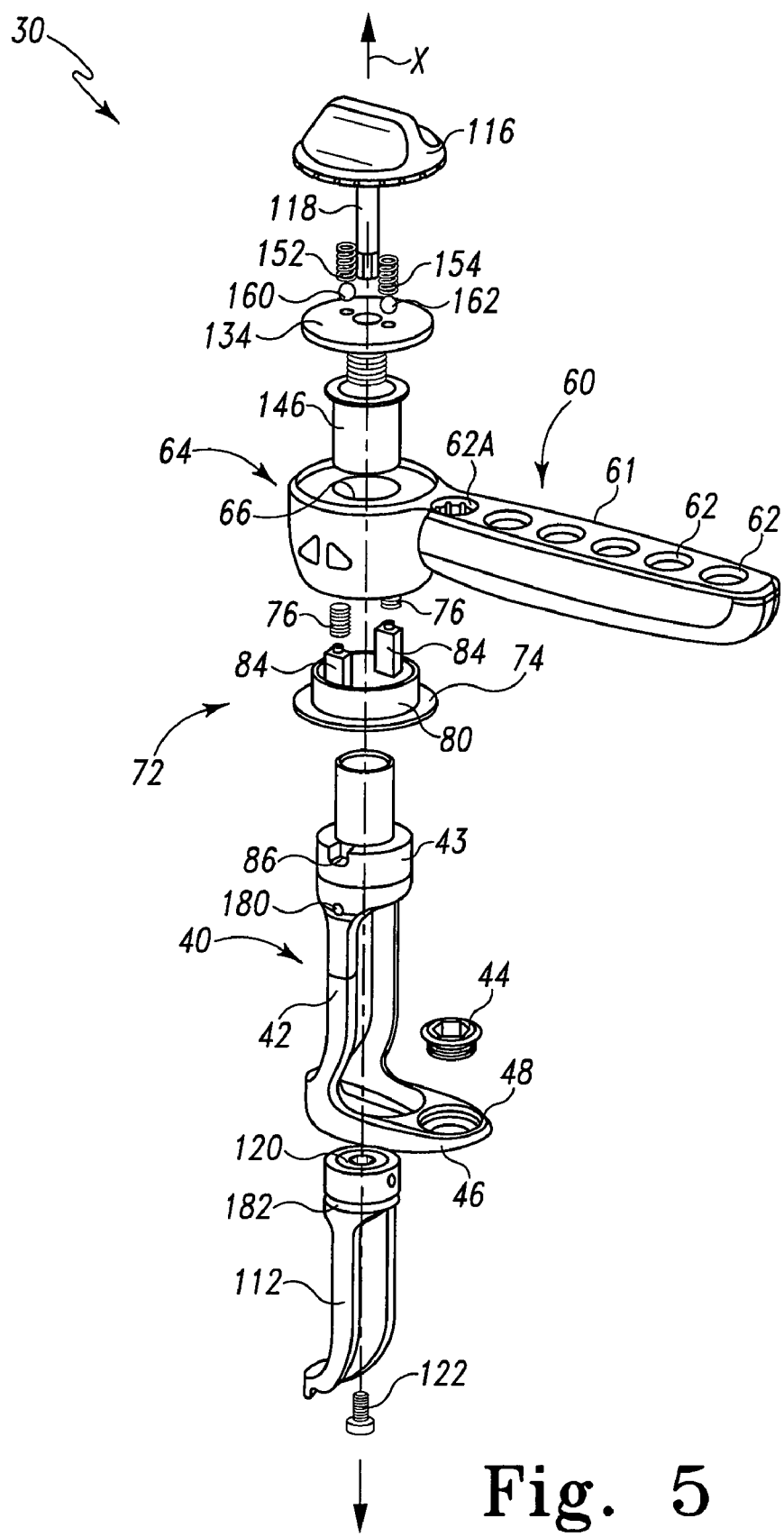
FIG. 5 is an exploded, perspective view of an instrument assembly (with the implant assembly not shown) that is used to implant the implant assembly of FIG. 1 in the patient in a minimally invasive manner according to the present disclosure.
Figure 6:
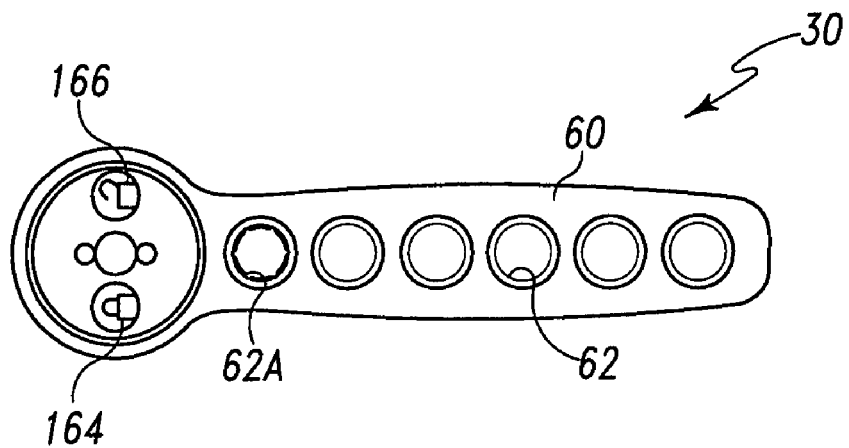
FIG. 6 is a top elevational view of the instrument assembly of FIG. 5, with the knob of the instrument assembly removed for clarity of viewing.
Figure 7:
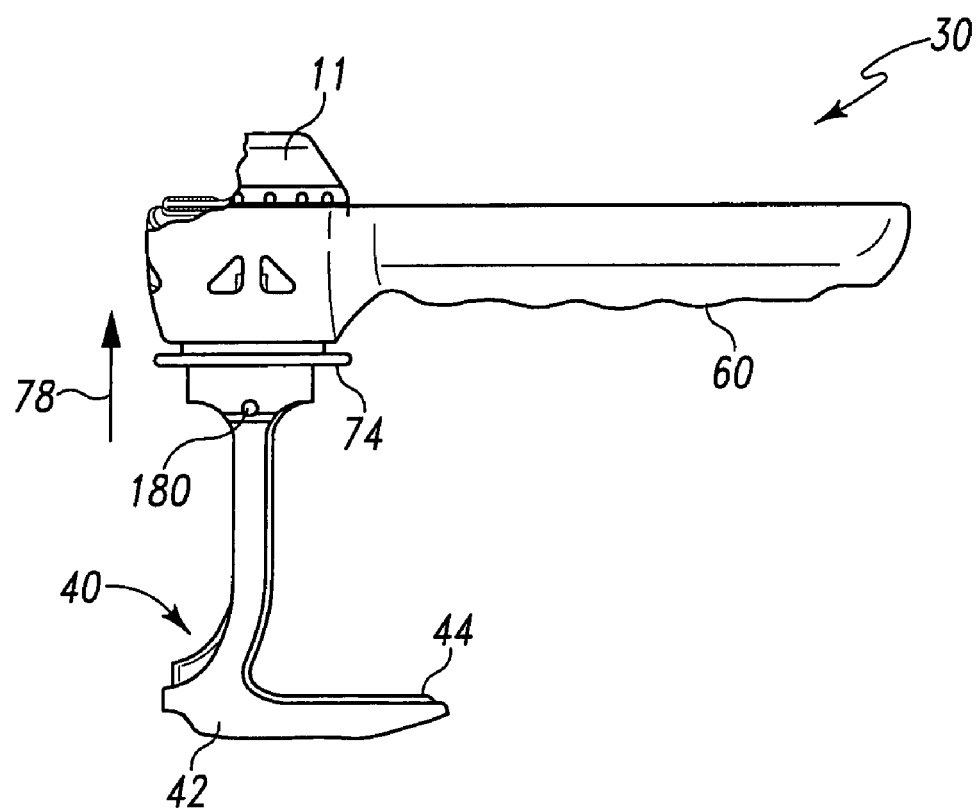
FIG. 7 is a side elevational view of the instrument assembly of FIG. 5, with the implant assembly not shown.
Figure 8:
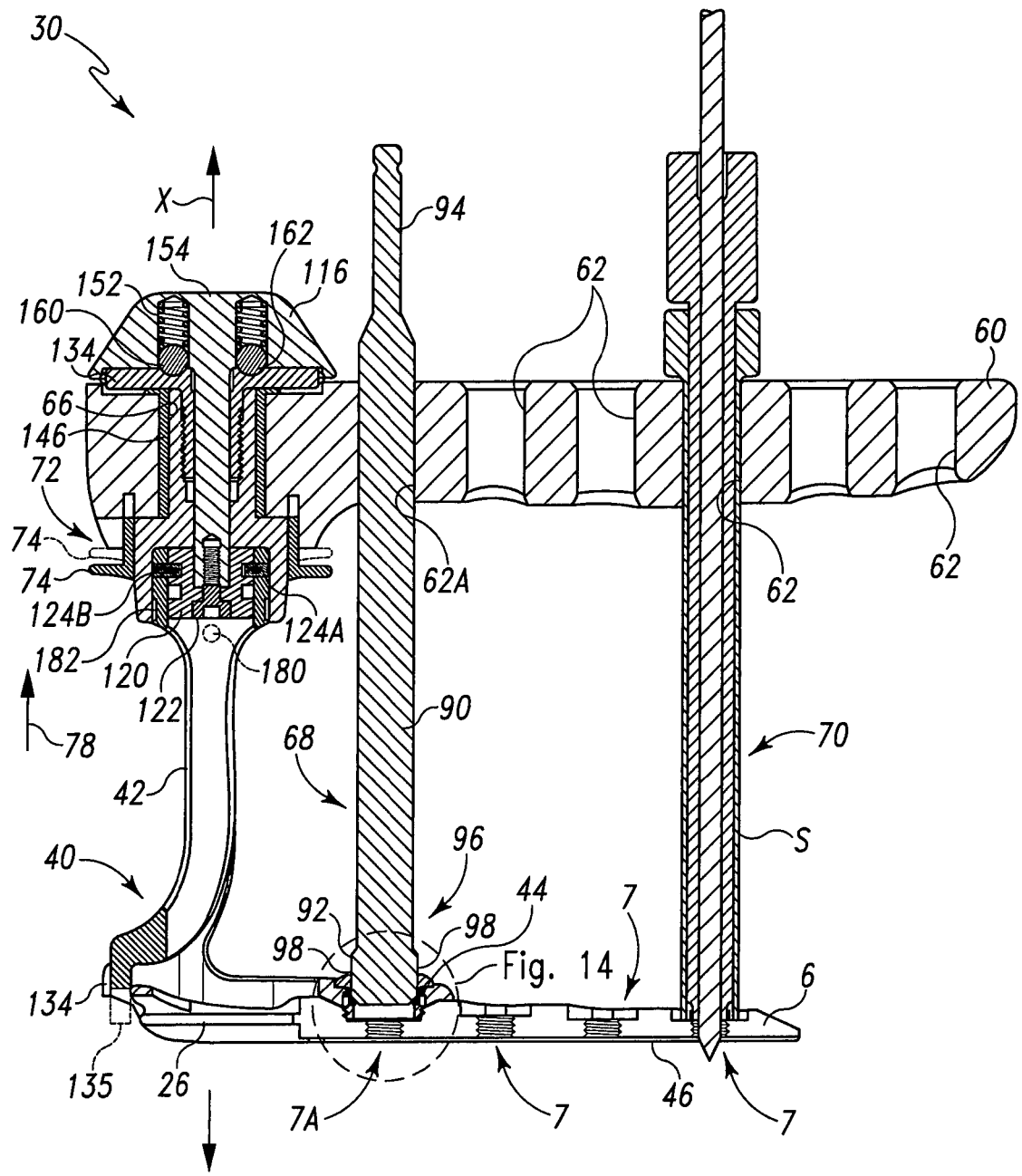
FIG. 8 is a cross sectional view of the instrument assembly of FIG. 5, with the implant assembly shown.

Turning now to FIGS. 5-7, there is shown an instrument assembly 30 that is used to facilitate implantation of the bone plate 6 and the bone screws 8A, 8B of the implant assembly 2 into the patient P. FIG. 8 also shows the instrument assembly 30, and a couple of other devices supported thereby.

Figure 14:
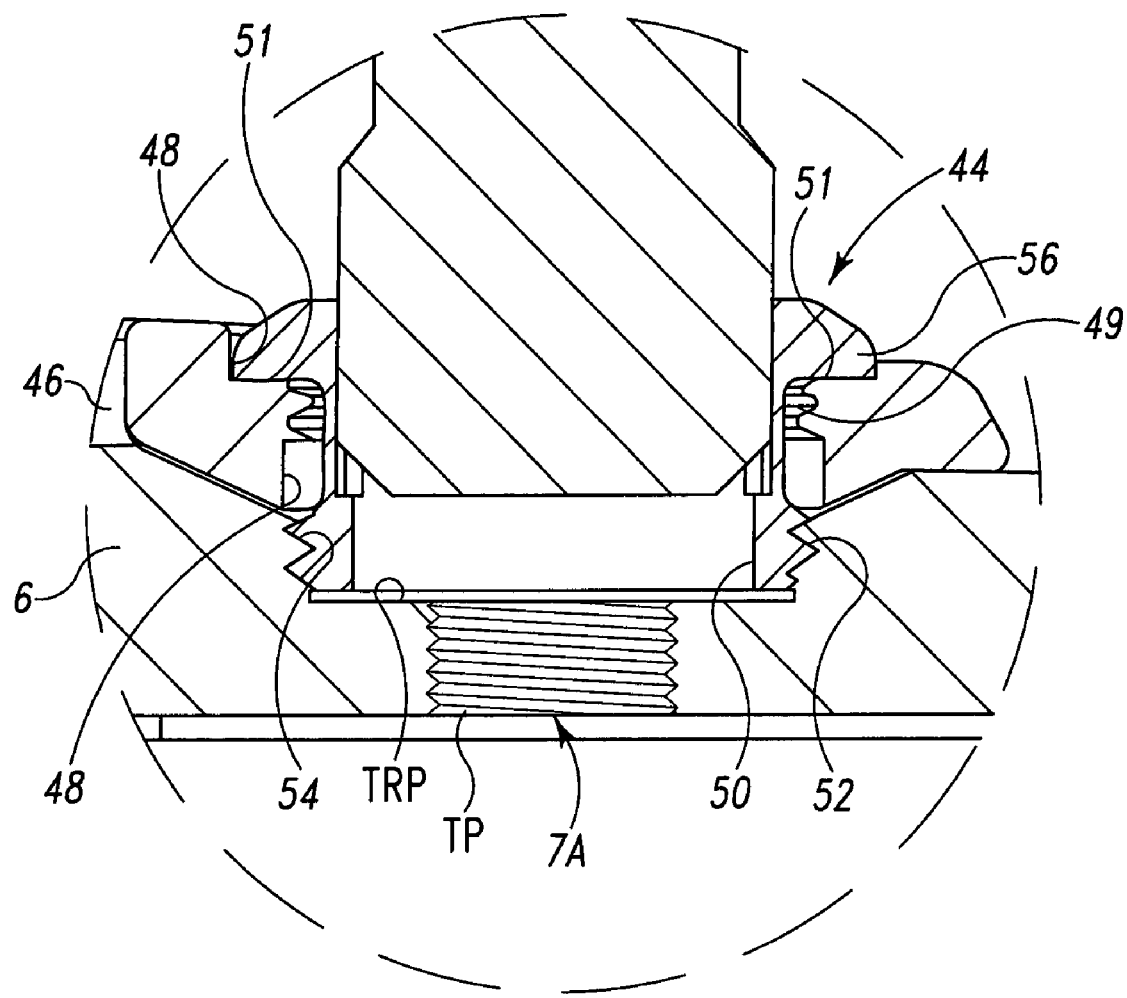
FIG. 14 is an enlarged, fragmentary, cross sectional view of the instrument assembly showing the portion of FIG. 8 that is encircled and identified as FIG. 14.

The instrument assembly 30 includes a plate holder 40 having a body 42 and a coupling component 44 rotatably supported by the body 42. The body 42 is also shown in FIGS. 9-10, while the coupling component 44 is also shown in FIGS. 11-13. The body 42 includes a foot portion 46 that defines a passage 48. The body 42 further includes a neck 43. The foot portion 46 includes a set of internal threads 49 located within the passage 48 as shown in FIG. 14. The coupling component 44 has defined therein a passage 50 extending therethrough. The coupling component 44 includes a flange 45 and a set of external threads 52 that is configured to meshingly engage with the set of internal threads 49 of the foot portion 46. The set of external threads 52 of the coupling component 44 is also configured to meshingly engage with a set of internal threads 54 defined in the bone plate 6 as shown in FIG. 14.

In order to assemble the coupling component 44 to the foot portion 46, the coupling component 44 is advanced into the passage 48 of the foot portion until the set of external threads 52 of the coupling component 44 contact the set of internal threads 49 of the foot portion 46. Thereafter, the coupling component 44 is rotated so that the set of external threads 52 meshing engagement with the set of internal threads 49 of the foot portion 46. Continued rotation of the coupling component 44 in relation to the foot portion 46 results in advancement of the set of external threads 52 through the set of internal threads 49. After the set of external threads 52 are advanced through the set of internal threads 49, the coupling component 44 is rotatably attached to the foot portion 46. In this assembled state, the coupling component 44 is able to rotate freely in relation to the foot portion 46. Further, the coupling 44 is able to move a distance axially within the passage 48, but is prevented from becoming detached from the foot portion 46. Indeed, upward movement of the coupling component 44 in relation to the foot portion 46 is limited by interaction of the set of external threads 52 of the coupling component and the set of internal threads 49 of the foot portion. Also, downward movement of the coupling component 44 in relation to the foot portion 46 is limited by interaction of the flange 56 of the coupling component and a shoulder 51 of the foot portion which is located in the passage 48.

Note that when the set of external threads 52 of the coupling component 44 are mated with the set of internal threads 54 of the bone plate 6, the bone plate 6 is secured to the foot portion 44 of the plate holder 40. Also note that when the set of external threads 52 of the coupling component 44 are mated with the set of internal threads 54 of the bone plate 6, the passageway 50 of the coupling component 44 is aligned with the fastener opening 7A of the bone plate 6.

Figure 15:
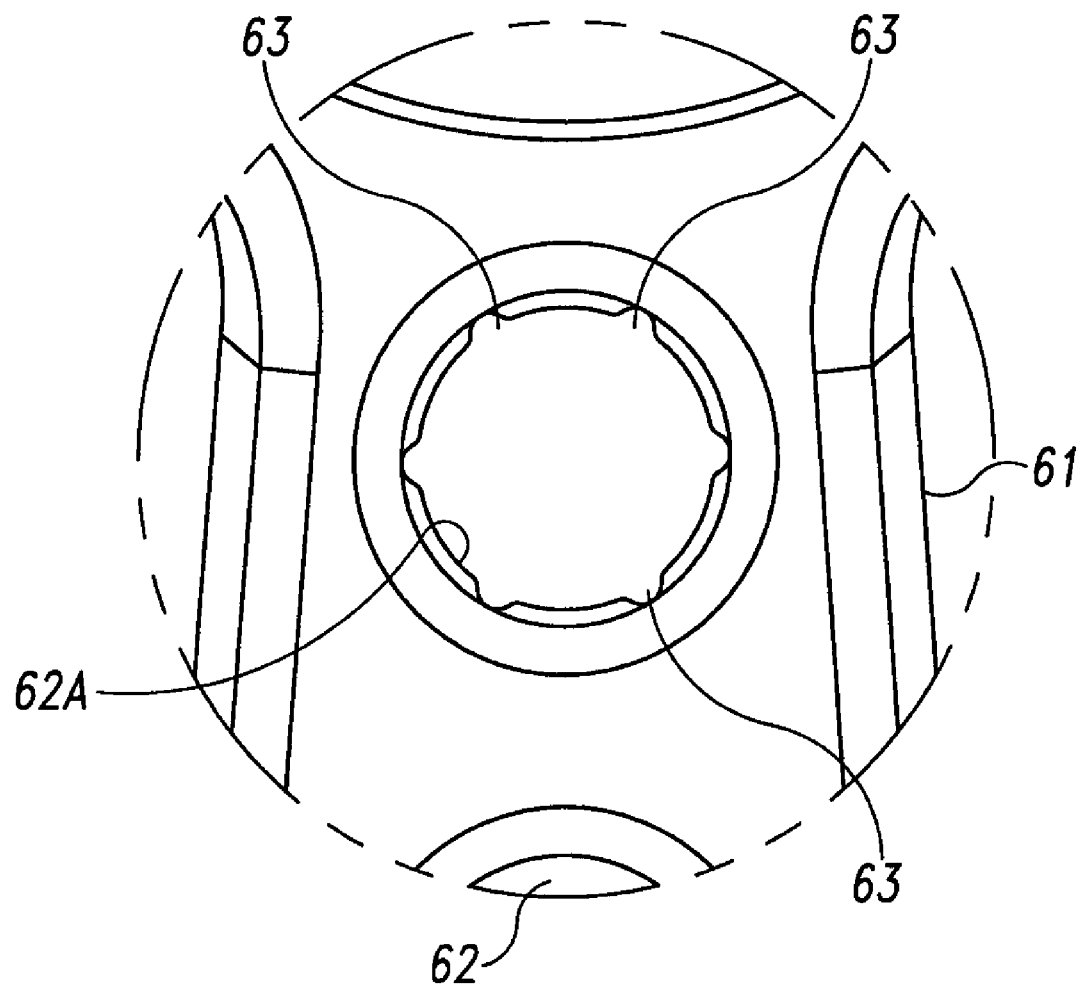
FIG. 15 is an enlarged, fragmentary, top elevational view of the guide component of the instrument assembly of FIG. 5.
Figures 23, 24:
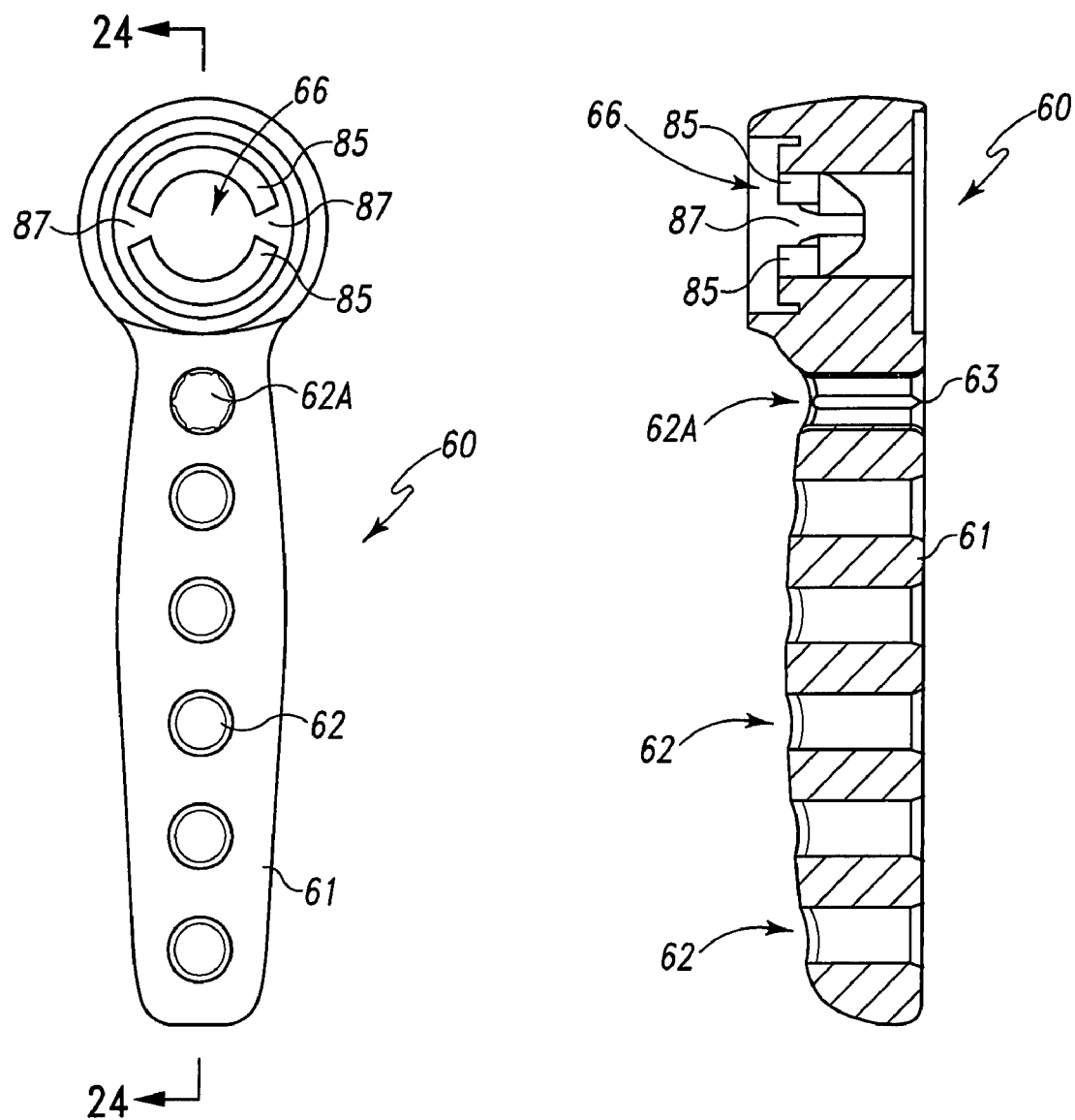
FIG. 23 is a bottom elevational view of a guide component of the instrument assembly of FIG. 5.
FIG. 24 is a cross sectional view of the guide component taken along the line 24-24 of FIG. 23.

As shown in FIGS. 5-8, the instrument assembly 30 further includes a guide component 60 that is pivotably secured to the body 42 of the plate holder 40. The guide component 60 includes a handle portion 61 having defined therein a plurality of guide holes 62, 62A. The handle portion further defines a plurality of peripheral slots 63 that are located in the guide hole 62A as shown in FIGS. 5 and 15. The guide component 60 further includes an end portion 64 that includes a cavity 66 defined therein as shown in FIGS. 23-24.

Figure 16:
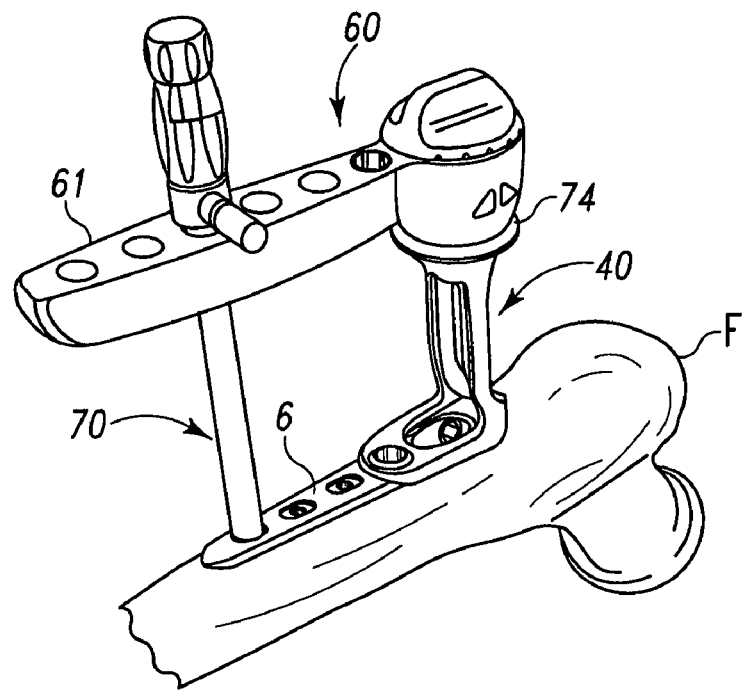
FIG. 16 is a perspective view of the instrument assembly of FIG. 5 (with the implant assembly attached thereto) and being used to implant the implant assembly in a femur according to the present disclosure, with the femur and the implant assembly being shown removed from the body of a patient P for clarity of viewing.
Figure 17:
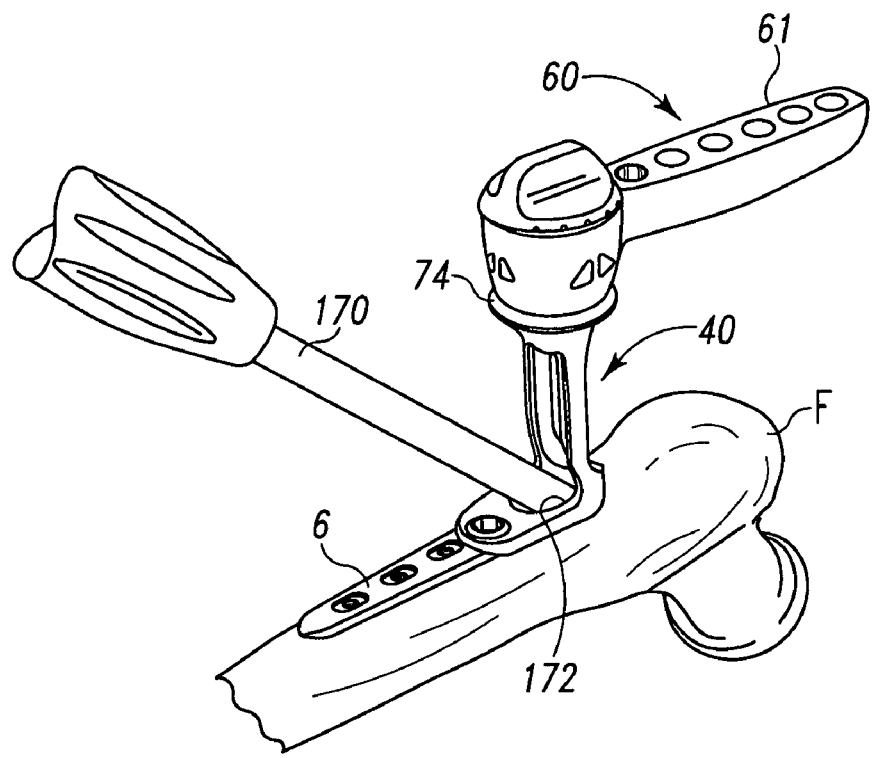
FIG. 17 is another perspective view of the instrument assembly of FIG. 5 (with the implant assembly attached thereto) and being used to implant the implant assembly in a femur according to the present disclosure, with the femur and the implant assembly being shown removed from the body of a patient P for clarity of viewing.
Figures 18, 19:
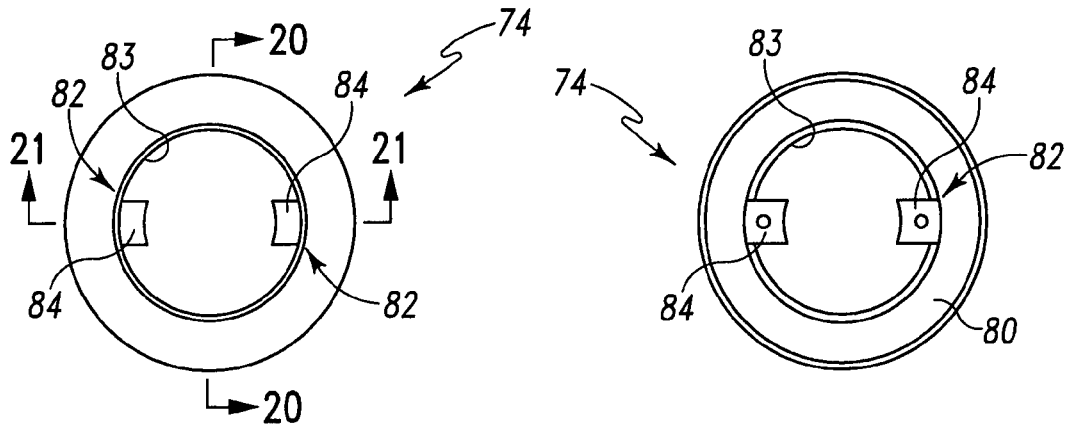
FIG. 18 is a bottom elevational view of an actuator of the instrument assembly of FIG. 5.
FIG. 19 is a top elevational view of the actuator of FIG. 18.
Figures 20, 21:
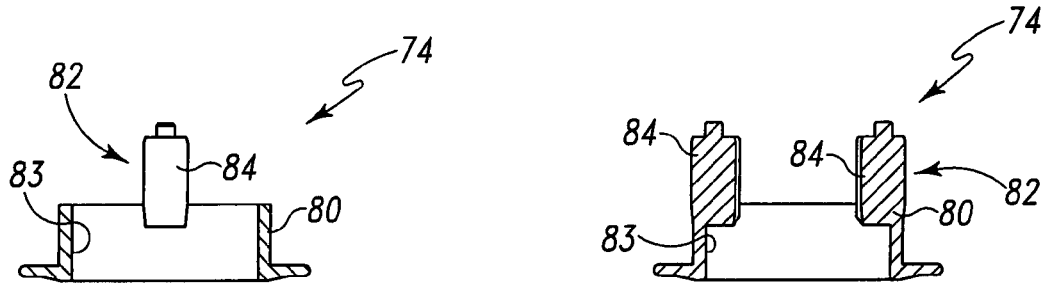
FIG. 20 is a cross sectional view of the actuator taken along the line 20-20 of FIG. 18.
FIG. 21 is a cross sectional view of the actuator taken along the line 21-21 of FIG. 18.

Since the guide component 60 is pivotably connected to the plate holder 40, the guide component 60 is movable in relation to the body 42 of the plate holder 40 between a first position shown in FIG. 16 (see also FIGS. 7-8) and a second position shown in FIG. 17. The guide component 60 pivots about an axis X. (See FIGS. 5 and 8.) Pivoting the guide component 60 180° about the axis X causes the guide component 60 to move from its first position (see FIG. 16) to its second position (see FIG. 17).

When the guide component 60 is located at its first position in relation to the plate holder 40 (see FIG. 16), the plurality of guide holes 62, 62A are respectively aligned with the plurality of fastener openings 7, 7A. For example, as shown in FIG. 8, the left most guide hole 62A is aligned with the left most fastener opening 7A so that an elongate instrument (e.g. a driver 68) may be advanced through the guide hole 62A and present its working end at the fastener opening 7A. Further, for example, as shown in FIG. 8, the fourth guide hole 62 (from the left) is aligned with the fourth fastener opening 7 (from the left) so that an elongate instrument (e.g. a drill assembly 70) may be advanced through the guide hole 62 and present its working end at the fastener opening 7. When the guide component 60 is located at its second position in relation to the plate holder 40 (see FIG. 17), the plurality of guide holes 62, 62A are respectively misaligned with the plurality of fastener openings 7, 7A. Indeed, advancing elongate instruments 68, 70 respectively through the guide holes 62, 62A would not result in the working ends of the elongate instruments being respectively presented at the fastener openings 7, 7A.

Moreover, as can be seen from FIGS. 16 and 17, when the guide component 60 is positioned at its first position in relation to the plate holder 40 (see FIG. 16), the handle portion 61 is positioned over the bone plate 6. On the other hand, when the guide component 60 is positioned at its second position in relation to the plate holder 40 (see FIG. 17), the handle portion 61 is not positioned over the bone-plate 6. Positioning of the guide component 60 at its second position (see FIG. 17) facilitates visibility of the bone plate 6 and surrounding area. Moreover, positioning of the guide component 60 at its second position (see FIG. 17) facilitates access of instruments and other devices to the bone plate 6 and surrounding area.

Figure 22:
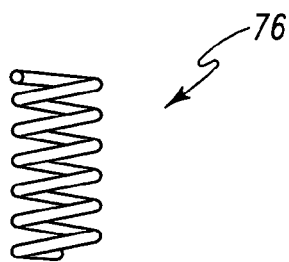
FIG. 22 is a side elevational view of a spring 76 of the instrument assembly of FIG. 5.

The instrument assembly 30 further includes a locking mechanism 72 that is configured to lock the guide component 60 in relation to the body 42 of the plate holder 40 at its first position as shown in FIG. 16, and at its second position as shown in FIG. 17. The locking mechanism 72 includes an actuator 74 that is partially located in the cavity 66 of the guide component 60. The actuator 74 is movable between a lower position (shown in solid in FIG. 8), and an upper position (shown in phantom in FIG. 8). The locking mechanism 72 includes a plurality of springs 76 configured to bias the actuator 74 toward its lower position. (See FIG. 8.) The springs 76 have an identical configuration with respect to each other, and one spring 76 is shown in FIG. 22. The springs 76 are located in the cavity 66 of the guide component 60. Within the cavity 66, the springs 76 are interposed between the actuator 74 and the guide component 60. In order to move the actuator 74 from its lower position to its upper position against the spring bias of the springs 76, force is applied to the actuator in the direction of arrow 78 thereby urging the actuator upwardly until the actuator 74 contacts a lower surface of the guide component 60. Thereafter, in order to move the actuator 74 from its upper position to its lower position, the upwardly applied force is removed thereby allowing the springs 76 to urge the actuator 74 downwardly to its lower position.

When the actuator 74 is positioned in its lower position, the guide component 60 is locked in relation to the body 42 of the plate holder 40 at its first position (shown in FIG. 16). Thereafter, an upward force is applied to the actuator 74 in the direction of arrow 78 thereby moving the actuator from its lower position (shown in solid in FIG. 8) to its upper position (shown in phantom in FIG. 8). When the actuator 74 is positioned in its upper position, the guide component 60 is free to rotate in relation to the body 42 of the plate holder. Force is then applied to the guide component 60 so that the guide component 60 pivots 1800 about the axis X causing the guide component 60 to move from its first position (shown in FIG. 16) to its second position (shown in FIG. 17). Thereafter, the upward force is removed from the actuator 74 thereby allowing the springs 76 to urge the actuator 74 downwardly to its lower position. When the actuator 74 is positioned in its lower position, the guide component 60 is locked in relation to the body 42 of the plate holder 40 at its second position (shown in FIG. 17).

As shown in FIGS. 18-21, the actuator 74 includes a body 80 and a blocking structure 82 supported by the body 80. The body 80 defines a passage 83 therethrough. The blocking structure 82 includes a number of detents 84 attached to the body 80. The body 42 of the plate holder 40 has defined therein a number of detent recesses 86. (See FIGS. 5 and 9.) As shown in FIGS. 23-24, the guide component 60 includes a number of internal walls 85 that are positioned within the passage 66. The internal walls 85 define a number of slots 87.

When the instrument assembly 30 is in an assembled state, the body 80 of the actuator 74 is positioned around the neck 43 of the plate holder 40 so that the neck 43 extends through the passage 83 of the body 80 of the actuator 74 as shown in FIG. 8. The detents 84 are located within the slots 87 of the guide component 60. Thus, the actuator 74 is able to move in the direction of axis X since the detents 84 are able slide axially within the slots 87, however, the internal walls 85 of the guide component 60 prevent rotation of the actuator 74 in relation to the guide component 60. Thus, the actuator 74 is rotationally fixed in relation to the guide component 60.

When the actuator 74 is positioned at its lower position (shown in solid in FIG. 8), the blocking structure 82 is located in the number of detent recesses 86. In particular, one detent 84 is positioned in one detent recess 86, while another detent 84 is positioned in another detent recess 86. As a result, rotation of the actuator 74 in relation to the body 42 of the plate holder 40 is prevented when the actuator 74 is positioned at its lower position. And since the actuator 74 is rotationally fixed in relation to the guide component 60, the guide component 60 is prevented from rotating in relation to the body 42 of the plate holder 40 when the actuator 74 is positioned at its lower position.

In contrast, when the actuator 74 is positioned at its upper position (shown in phantom in FIG. 8), the blocking structure 82 is spaced apart from the number of detent recesses 86. In particular, both detents 84 are spaced apart from both detent recesses 86. Therefore, rotation of the actuator 74 in relation to the body 42 of the plate holder 40 is allowed when the actuator 74 is positioned at its upper position. Thus, the guide component 60 is allowed to be rotated in relation to the body 42 of the plate holder 40 when the actuator 74 is positioned at its upper position. Accordingly, when the actuator 74 is positioned at its upper position, the guide component 60 may be rotated from its position shown in FIG. 16 to its position shown in FIG. 17. Furthermore, when the actuator 74 is positioned at its upper position, the guide component 60 may be rotated from its position shown in FIG. 17 to its position shown in FIG. 16.

Turning again to FIG. 8, the instrument assembly 30 further includes the driver 68. The driver 68 includes a shaft 90. The driver 68 further includes a tip portion 92 attached to the shaft 90 at one end, and a drive portion 94 attached to the shaft 90 at the other end. The drive portion 94 includes a flat drive surface (not shown). The drive portion 94 is configured to be coupled to a chuck of a manual or power drill (not shown). The tip portion 92 includes a drive structure 96. The drive structure 96 includes a plurality of spaced apart linearly extending ribs 98 (see FIG. 8). Note that the coupling component 44 includes a drive structure 100 (see FIGS. 12-13) that is configured to mate with the drive structure 96 of the tip portion 92 when the tip portion 92 is positioned within the passageway 50 of the coupling component 44 as shown in FIG. 8. The drive structure 100 defines a plurality of spaced apart linearly extending slots 102 that is configured to receive respectively the plurality of spaced apart linearly extending ribs 98. It should be appreciated that the slots 102 extend from a proximal end of the coupling component 44 towards the distal end of the coupling component, and terminates prior to arriving at the distal end of the coupling component 44 as shown in FIG. 13. Further, the tip portion 92 of the driver 68 is configured to interact with the structure of the coupling component 44 that defines the slots 102 so that the tip portion 92 of the driver 68 is prevented from being advanced entirely through the passageway 50 of the coupling component 44.

In order to utilize the driver 68 to attach the bone plate 6 to the plate holder 40, the tip portion 92 of the driver needs to be mated with the drive structure 100 of the coupling component 44. To this end, the tip portion 92 is advanced through the guide hole 62A of the guide component 60. As stated above, the handle portion 61 defines a plurality of peripheral slots 63 that are located in the guide hole 62A as shown in FIGS. 5 and 15. In order to advance the tip portion 92 through the guide hole 62A, the plurality of spaced apart ribs 98 of the tip portion are aligned with the plurality of peripheral slots of the handle portion 61. Thereafter, the tip portion 92 is advanced through the guide hole 62A so that the drive structure 96 passes through the peripheral slots 63. Note that the other guide holes 62 of the guide component 60 are not similarly slotted, and are configured to prevent advancement of the tip portion 92 through the guide holes 62. Continued advancement of the tip portion 92 toward the bone plate 6 results in the tip portion 92 being received within the passage 50 of the coupling component 44. When the tip portion 92 is received within the passage 50, the drive structure 96 of the driver 68 is mated with the drive structure 100 of the coupling component 44. When the drive structure 96 of the driver 68 is mated with the drive structure 100 of the coupling component 44, the shaft 90 of the driver 68 extends through the guide hole 62A of the guide component 60.

In order to secure the bone plate 6 to the plate holder 40, the set of external threads 52 of the coupling component 44 of the plate holder 40 are meshingly engaged with the set of internal threads 54 of the bone plate 6. This is accomplished by placing the driver 68 through the guide hole 62A of the guide component 60 and advancing the tip portion 92 of the driver 68 toward the coupling component 44 until the drive structure 96 of the tip portion 92 mates with drive structure 100 of the coupling component 44. Thereafter, the driver 68 is rotated thereby causing the coupling component 44 to be rotated in relation to the bone plate 6. Rotation of the coupling component 44 in relation to the bone plate 6 causes the set of external threads 52 of the coupling component 44 to be meshingly engaged with the set of internal threads 54 of the bone plate 6 thereby securing the bone plate 6 to the plate holder 40.

Figure 25:
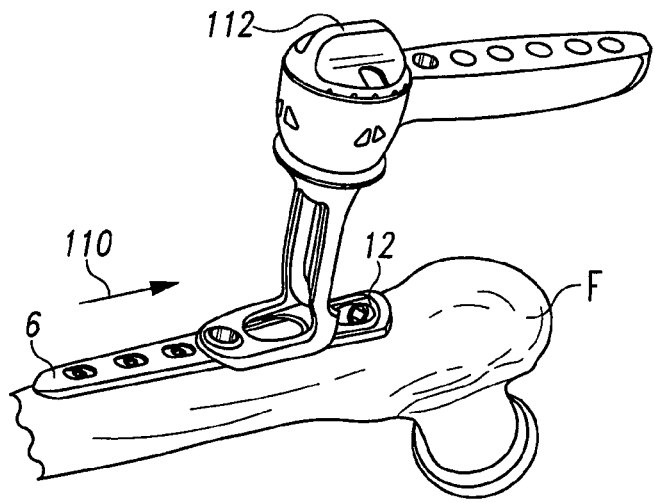
FIG. 25 is a perspective view of the instrument assembly of FIG. 5 (with the implant assembly also shown) and being used to implant the implant assembly in a femur according to the present disclosure, with the femur and the implant assembly being shown removed from the body of a patient P for clarity of viewing (note that the bone plate and fastener guide are shown in an unseated state)
Figure 26:
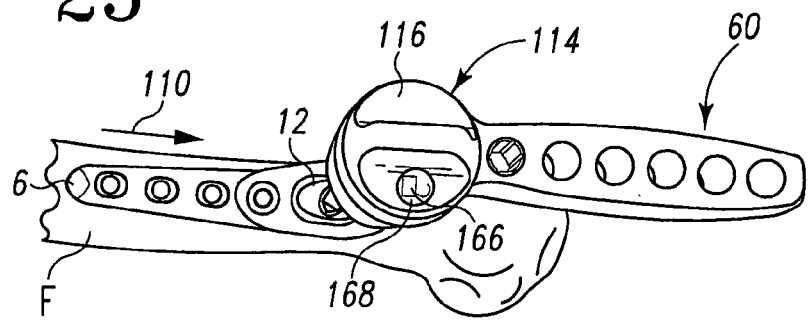
FIG. 26 is another perspective view of the instrument assembly of FIG. 5 (with the implant assembly also shown) and being used to implant the implant assembly in a femur according to the present disclosure, with the femur and the implant assembly being shown removed from the body of a patient P for clarity of viewing (note that the bone plate and fastener guide are shown in a seated state) (also note that the knob 116 is shown in a first position in which the "unlocked" icon is displayed)

After the lag screw assembly 4 is secured within a femoral head, neck, and shaft of the femur F of the patient P as shown in FIG. 4, a surgeon manipulates the plate holder 40 (with the bone plate 6 attached thereto) so that the bone plate 6 is advanced through the incision I to a position on the femur F that is spaced apart from the lag screw assembly 4 as shown in FIG. 25. Thereafter, the plate holder 40 is further manipulated to advance the bone plate 6 in the direction of arrow 110 to a position on the femur F in which the seating surface SS1 of the fastener guide 12 is positioned in contact with the seating surface SS2 of the bone plate 6 as shown in FIG. 26. (See also FIG. 1 showing the bone plate 6 seated against the fastener guide 12.) During such advancement of the bone plate 6 in the direction of arrow 110, the fastener guide 12 is advanced through the access opening 29 defined in the bone plate 6. Further, during such advancement of the bone plate 6 in the direction of arrow 110, the projection 26 of the bone plate 6 is mated with the channel 24 of the fastener guide 12. When the seating surface SS2 of the bone plate 6 is positioned in contact with the seating surface SS1 of the fastener guide 12, the bone plate and the fastener guide are in a seated state (shown in FIG. 26). In contrast, when the seating surface SS2 of the bone plate 6 is spaced apart from the seating surface SS1 of the fastener guide 12, the bone plate and the fastener guide are in an unseated state (shown in FIG. 25).

The instrument assembly 30 is operable to verify whether the bone plate 6 and the fastener guide 12 are in a seated state (i.e. the seating surface SS1 of the fastener guide 12 is located in contact with a seating surface SS2 of the bone plate 6) when the bone plate 6 is attached to the plate holder 40 as shown in FIG. 26. In particular, the instrument assembly 30 includes a stop structure 112 that is movable in relation to the body 42 of the plate holder 40 between an upper position (shown in FIG. 8) and a lower position (shown in FIG. 27). The instrument assembly 30 also includes an actuator 114 that is movable between a first position shown in FIG. 26 to a second position shown in FIG. 28. The actuator 114 includes a knob 116, a shaft 118, a cam 120, and a fastener 122 as shown in FIGS. 8 and 29. The shaft 118 is attached to the knob 116 since the shaft 118 and the knob are integrally molded together as one part. The cam 120 is attached to a distal end of the shaft 118 by the fastener 122. In particular, the cam 120 includes a central passage in which the distal portion of the shaft 118 is positioned. The distal portion of the shaft 118 includes an internally threaded recess. The fastener 122 is threadingly received within the internally threaded recess of the shaft 118 to secure the cam 120 to the shaft 118. When the instrument assembly 30 is assembled as shown in FIG. 8, rotation of the knob 116 causes rotation of the cam 120.

Figure 29:
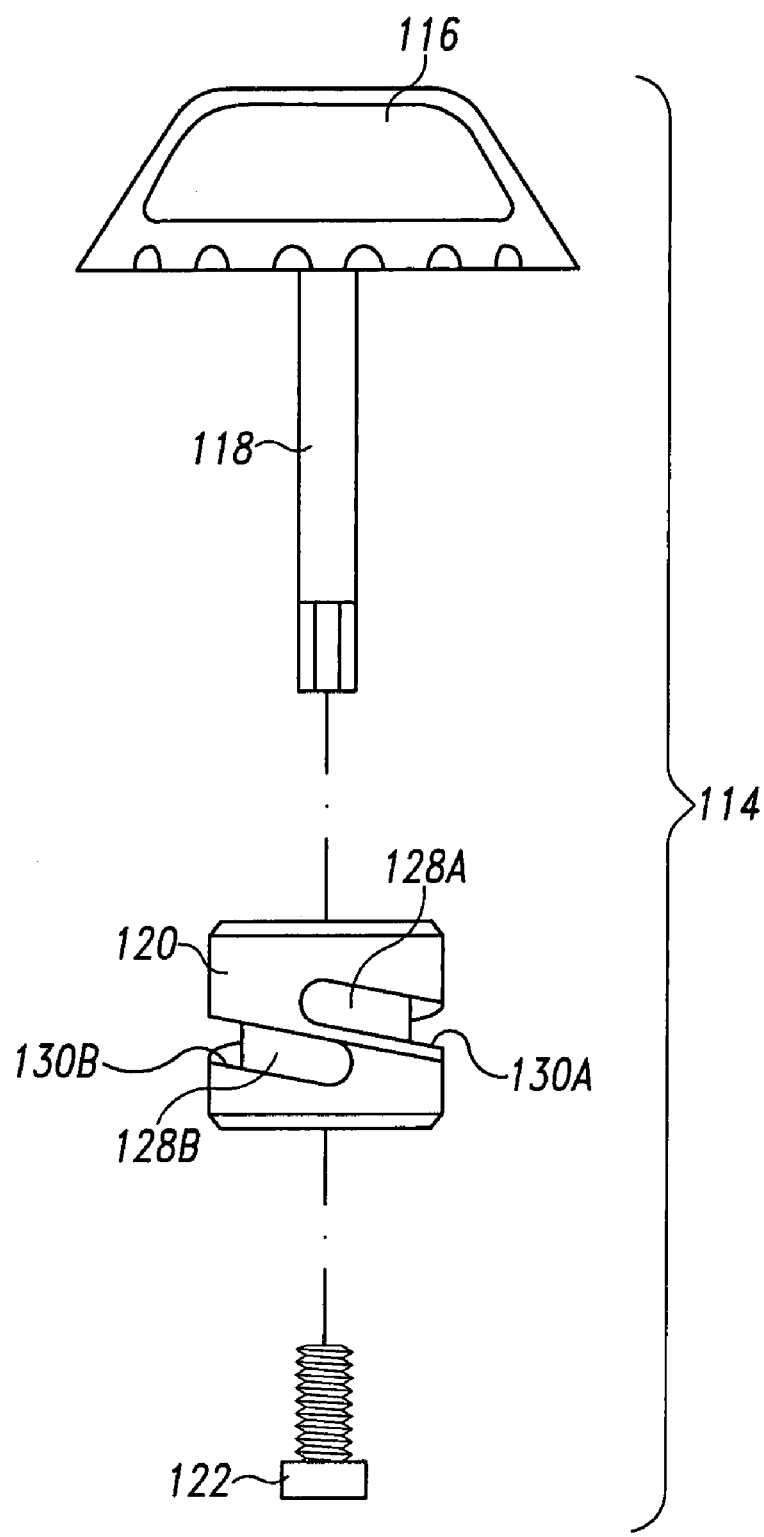
FIG. 29 is an exploded, perspective view of the actuator of the instrument assembly of FIG. 5.
Figure 30:
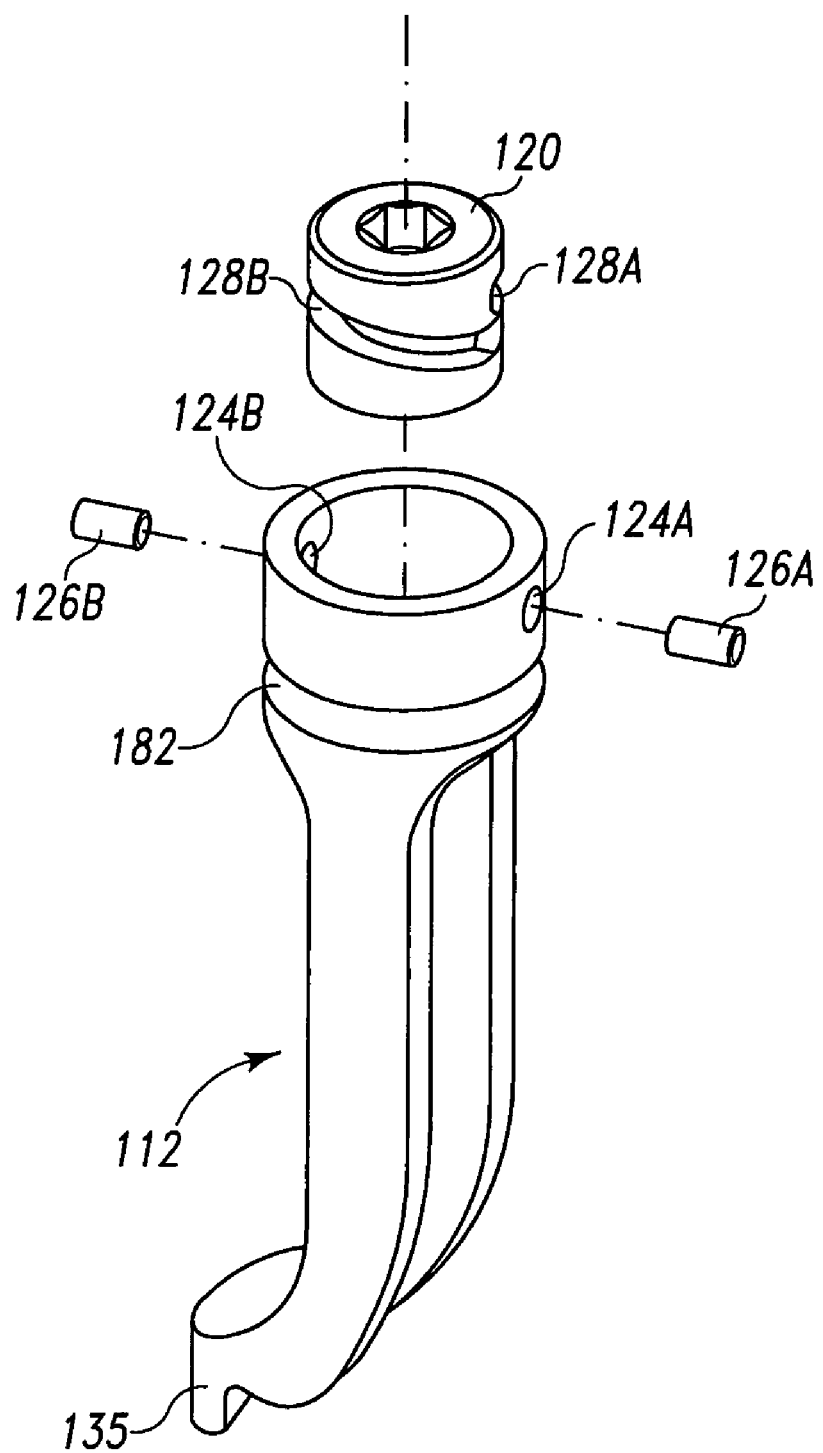
FIG. 30 is an exploded, perspective view of the cam, cam riders, and stop structure of the instrument assembly of FIG. 5.

The stop structure 112 has defined therein a number of holes 124A, 124B as shown in FIG. 30. The stop structure 112 further includes a number of cam riders 126A, 126B each being secured within a respective hole 124A, 124B, yet partially projecting from the respective hole 124A, 124B as shown in FIG. 8. The cam 120 has defined therein a cam track 128A and a cam track 128B. The cam track 128A defines a cam surface 130A, while the cam track 128B defines a cam surface 130B as shown in FIG. 29. When the instrument assembly 30 is assembled, the cam rider 126A is positioned within the cam track 128A and contacts the cam surface 130A, while the cam rider 126B is positioned within the cam track 128B and contacts the cam surface 130B. Rotation of knob 116 causes rotation of the cam 120. In turn, rotation of the cam 120 causes movement of the stop structure 112 in the direction of the axis X due to the interaction between the cam riders 126A, 126B and the cam surfaces 130A, 130B. Rotation of the knob 116 in a clockwise direction causes the stop structure 112 to move downwardly in a path of movement in the direction of the axis X, while rotation of the knob 116 in a counter-clockwise direction causes the stop structure 112 to move upwardly in the path of movement in the direction of the axis X. (See FIG. 8.)

The stop structure 112 includes a tang 135 located at the distal portion thereof. Downward movement of the stop structure 112 in its path of movement from its upper position (shown in FIG. 8) to its lower position (shown in FIG. 27), causes downward movement of the tang 135 from its upper position (shown in solid in FIG. 8) to its lower position (shown in FIG. 27). Note the phantom depiction of the tang 135 in FIG. 8 also shows the tang 135 at its lower position.

It should be appreciated that if the bone plate 6 and the fastener guide 12 were positioned in an unseated state as shown in FIG. 25, downward movement of the stop structure 112 would be prevented due to the presence of the fastener guide 12 in the path of movement of the tang 135 of the stop structure 112. Indeed, the fastener guide 12 would block the downward movement of the stop structure. Thus, if a surgeon is attempting to rotate the knob 116 from its first position (shown in FIG. 26) to its second position (shown in FIG. 28) and rotation of the knob 116 is prevented at some point therebetween, the surgeon would have positive verification that the bone plate 6 and the fastener guide 12 are in an unseated state.

On the other hand, if the bone plate 6 and the fastener guide 12 were positioned in a seated state as shown in FIG. 26, downward movement of the stop structure 112 would be allowed due to the lack of presence of the fastener guide 12 in the path of movement of the tang 135 of the stop structure. Indeed, the fastener guide 12 would not block the downward movement of the stop structure 112 since the fastener guide 12 would be spaced apart from the path of movement of the tang 135. Thus, if a surgeon rotates the knob 116 from its first position (shown in FIG. 26) to its second position (shown in FIG. 28) without complication, the surgeon would have positive verification that the bone plate 6 and the fastener guide 12 are in a seated state.

The knob 116 is rotatable about the axis X as shown in FIG. 8. Rotation of the knob 116 from its first position (shown in FIG. 26) 180° about the axis X to its second position (shown in FIG. 28) causes the stop structure 112 to move from its upper position (shown in FIG. 8) to its lower position (shown in FIG. 27).

Note that after the stop structure 112 is moved to its lower position (shown in FIG. 27), the tang 135 prevents movement of the bone plate 6 in relation to the fastener guide 12. Thus, the stop structure 112 locks the bone plate 6 and the fastener guide 12 in its seated state when the stop structure 112 is positioned in its lower position (shown in FIG. 27).

Figure 28:
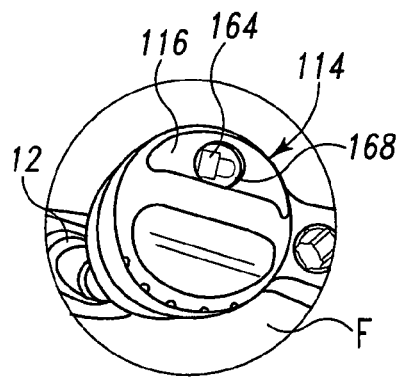
FIG. 28 is an enlarged, fragmentary, perspective view of the instrument assembly of FIG. 5 showing the knob 116 in a second position in which the "locked" icon is displayed.
Figure 31:
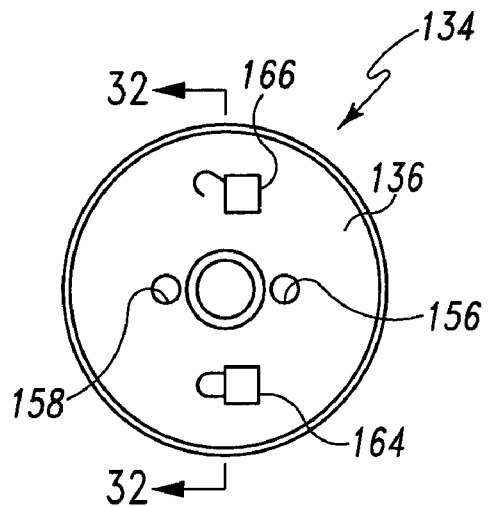
FIG. 31 is a top elevational view of the support member of the instrument assembly of FIG. 5.
Figure 32:
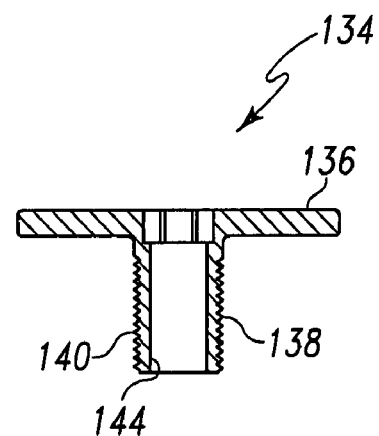
FIG. 32 is a cross sectional view of the support member taken along the line 32-32 of FIG. 31.

The instrument assembly 30 is configured to generate a tactile and audible indication of when the stop structure 112 is located at its upper position (shown in FIG. 26) and at its lower position (shown in FIG. 28). In particular, the instrument assembly 30 further includes a support member 134 that includes an upper portion 136 and a lower portion 138 as shown in FIGS. 31-32. (See also FIG. 8.) The lower portion 138 includes a set of external threads 140 that mate with a set of internal thread 142 defined in the neck 43 of the plate holder 40 as shown in FIG. 8. The support member 134 defines a passage 144 through which the shaft 118 of the actuator 114 extends. A sleeve 146 is positioned within the cavity 66 and surrounds both the neck 43 of the plate holder 40 and the lower portion 138 of the support member 134 as shown in FIG. 8.

Figure 33:
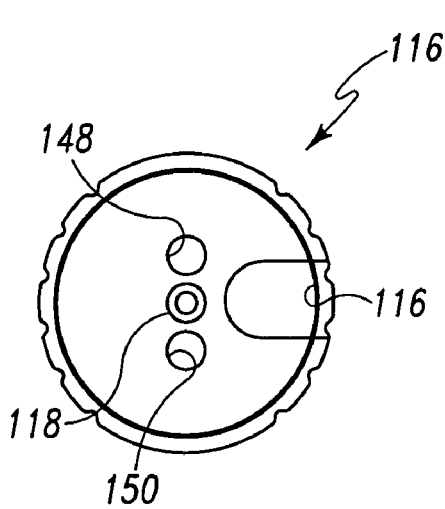
FIG. 33 is a bottom elevational view of the knob of the actuator of FIG. 29.
Figure 34:
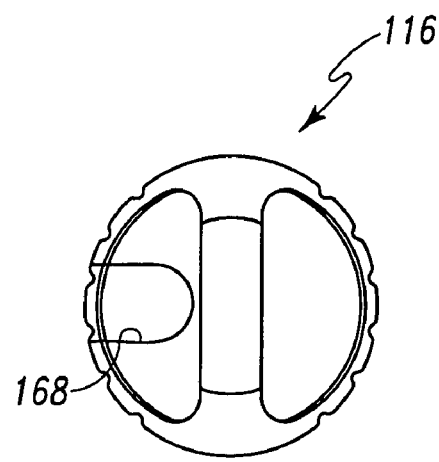
FIG. 34 is a top elevational view of the knob of the actuator of FIG. 29.

The knob 116 includes a spring recess 148 and a spring recess 150 as shown in FIGS. 33-34. A spring 152 is positioned in the spring recess 148, while a spring 154 is positioned in the spring recess 150. (See FIG. 5.) The upper portion 138 of the support member 134 has defined therein a detent recess 156 and a detent recess 158 as shown in FIGS. 31-32.

When the knob 116 is positioned in its first position (shown in FIG. 26), a ball detent 160 is interposed between the spring 152 and the detent recess 156 thereby resulting in the ball detent 160 being urged into the detent recess 156 as shown in FIG. 8. Similarly, when the knob 116 is positioned in its first position (shown in FIG. 26), a ball detent 162 is interposed between the spring 154 and the detent recess 158 thereby resulting in the ball detent 162 being urged into the detent recess 158 as shown in FIG. 8.

While the knob 116 is being rotated from its first position (shown in FIG. 26) to its second position (shown in FIG. 28), the ball detent 160 is advanced out of the detent recess 156 and is interposed between the spring 152 and the support member 134. Similarly, while the knob 116 is being rotated from its first position (shown in FIG. 26) to its second position (shown in FIG. 28), the ball detent 162 is advanced out of the detent recess 158 and is interposed between the spring 154 and the support member 134.

Then, when the knob 116 arrives so as to be positioned at its second position (shown in FIG. 28), the ball detent 160 becomes interposed between the spring 152 and the detent recess 158 thereby resulting in the ball detent 160 being urged into the detent recess 158. Similarly, when the knob 116 is positioned at its second position (shown in FIG. 26), the ball detent 162 becomes interposed between the spring 154 and the detent recess 156 thereby resulting in the ball detent 162 being urged into the detent recess 156.

Figure 27:
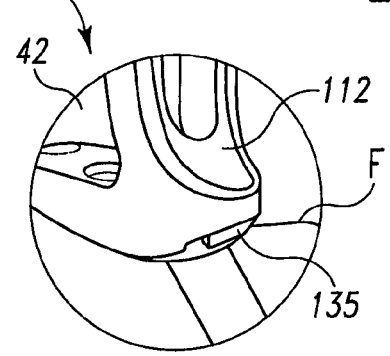
FIG. 27 is an enlarged, fragmentary, perspective view of the instrument assembly of FIG. 5, however, the stop structure 112 is shown positioned in its lower position.

When the knob 116 arrives so as to be positioned at its second position (shown in FIG. 28), a click sound is heard by the surgeon indicating that the stop structure 112 is now positioned at its lower position shown in FIG. 27. Similarly, when the surgeon rotates the knob 116 back to its first position (shown in FIG. 26) from its second position (shown in FIG. 28), arrival of the knob 116 at its first position (shown in FIG. 26) results in a similar click sound being heard by the surgeon. The click sounds are caused by the ball detents 160, 162 being urged into their respective detent recesses 156, 158 by their respective springs 152, 154.

In addition, the instrument assembly 30 is configured to provide a visual indication of when the stop structure 112 is located at its upper position (shown in FIG. 26) and at its lower position (shown in FIG. 28). In particular, the support member 134 includes a "locked" icon 164 and an "unlocked" icon 166 located on an upper surface of the upper portion 136 of the support member 134 as shown in FIG. 31. (See also FIG. 6.) The icons 164, 166 are preferably etched into an upper surface of the upper portion 136 of the support member 134. The icon 164 is preferably colored red, while the icon 166 is preferably colored green. Of course, other color schemes may be used. The knob 116 has defined therein a viewing opening 168 as shown in FIGS. 33-34. As shown in FIG. 26, when the knob 116 is positioned in its first position, the viewing opening 168 is positioned over the "unlocked" icon 166 thereby displaying the "unlocked" icon to the surgeon which informs the surgeon the stop structure 112 is now positioned at its upper position. On the other hand, as shown in FIG. 28, when the knob 116 is positioned in its second position, the viewing opening 168 is positioned over the "locked" icon 164 thereby displaying the "locked" icon to the surgeon which informs the surgeon the stop structure 112 is now positioned at its lower position.

Furthermore, the instrument assembly 30 is configured to provide an additional visual indication of when the stop structure 112 is located at its upper position (shown in FIG. 26) and at its lower position (shown in FIG. 28). In particular, the body 42 of the plate holder 40 has defined therein a number of viewing holes 180 as shown in FIGS. 9-10. The stop structure 112 defines a groove 182 that extends in a circumferential manner around the stop structure as shown in FIG. 30. The groove 182 is preferably colored red. Of course, the groove may be colored with a color other than red, such as yellow, pink, or orange. When the stop structure 112 is located at its upper position (shown in FIG. 26), the red-colored groove 182 of the stop structure 112 is hidden from view of a user of the instrument assembly 30 since the red-colored groove 182 is (i) located within the neck 43 of the body 42 of the plate holder 40, and (ii) located proximal to the viewing opening 180 defined in the body 42 of the plate holder 40. (See, e.g., FIG. 8, as well as, FIG. 7.) In contrast, when the stop structure 112 is located at its lower position (shown in FIG. 28), the red-colored groove 182 of the stop structure 112 is exposed to a user of the instrument assembly 30 since the red-colored groove is (i) located distal to the neck 43 of the body 42 of the plate holder 40, and (ii) aligned with the viewing openings 180 defined in the body 42 of the plate holder 40. (See, e.g., FIGS. 7 and 8.)

Thus, when the knob 116 is positioned in its first position as shown in FIGS. 8 and 26, the red-colored groove 182 is hidden from view thereby informing the surgeon the stop structure 112 is now positioned at its upper position. On the other hand, as shown in FIG. 28, when the knob 116 is positioned in its second position, the red-colored groove 182 is exposed to a user of the instrument assembly 30 which informs the surgeon the stop structure 112 is now positioned at its lower position.

Use of Instrumentation and Implant Components

Figure 35:
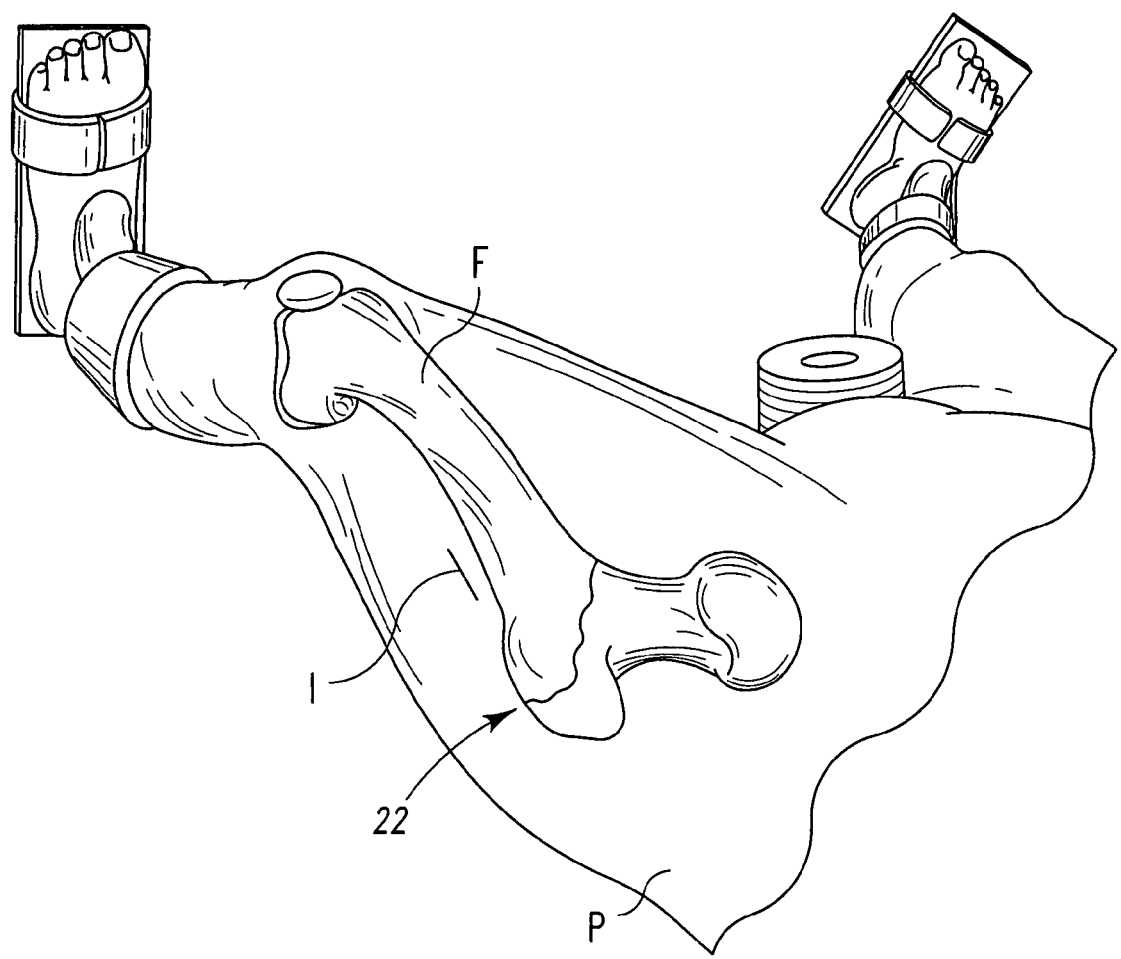
FIG. 35 is a fragmentary, perspective view of a patient with a fractured femur.

Use of the instrumentation and implant components described above facilitate reduction of a hip fracture in a minimally invasive manner. In particular, in order to perform such a procedure, a patient P is placed in a supine position on a standard fracture table. The fracture is then reduced and aligned using traction with external rotation followed by approximately 20 degrees of internal rotation to compress the fracture 22 (see FIG. 35). The reduction is then verified using dual-plane image intensification. The hip is then prepared and draped in a conventional manner.

Thereafter, an incision I is made that is 3-8 cm long (depending on the length of the bone plate being used) in the lateral aspect of the hip, with dissection beginning distal to the flare of the greater trochanter down to the vastus ridge and extending distally. (See FIG. 35.) The dissection is carried sharply down through the skin and subcutaneous tissue to the fascia lata. The fascia lata is split longitudinally thereby exposing the vastus lateralis. The vastus lateralis is then retracted anteriorly and the lateral aspect of the femoral shaft is then exposed.

The guide wire 200 is exteriorly placed adjacent to the femoral neck to assess lateral positioning and neck angle. The measuring device 210 (shown in FIGS. 39-42) may be used to determine the neck angle. The guide wire 200 is then advanced into the shaft, neck, and head of the femur F of the patient P. According to one embodiment of the disclosure, the measuring device 210 is used to guide advancement of the guide wire 200 into the femur F at a predetermined angle. In particular, as shown in FIG. 43, the guide wire 200 is positioned in the hook defined by the catch portion 226 of the catch 224 so that the guide wire 200 contacts the contact surface 230. As also shown in FIG. 43, the body 204 of the guide wire 200 is positioned in contact with the body 212 of the measuring apparatus 200. Thereafter, the guide wire 200 is aligned with a predetermined angle such as the 130° angle as indicated by the measurement indicia 222B on the measurement apparatus 210. (Note that various details of the measurement apparatus 210 is omitted from FIGS. 43-44 for clarity of viewing.) Then, the guide wire 200 is advanced into the shaft, neck, and head of the femur F under image intensification until its threads are secure to subchondral bone in the center of the femoral head in both anterior-posterior and lateral views.

After the guide wire 200 is advanced into the shaft, neck, and head of the femur F, the angle of the guide wire 200 with respect to the femur F may be verified with the measurement apparatus 210 positioned as shown in FIG. 43. Alternatively, if the guide wire 200 was advanced into the femur F without precise knowledge of its angle in relation to the femur F (e.g. such as would be the case if the measurement apparatus 210 was not used to guide advancement of the guide wire 200 into the femur F), the surgeon would then measure the angle of the guide wire 200 with respect to the femur F with the measurement apparatus 210 positioned as shown in FIG. 43. With the knowledge of the angle of the guide wire 200 with respect to the femur F, the surgeon can select a properly configured barrel (or fastener guide) of a lag screw assembly for subsequent implantation into the femur F.

Figure 44:
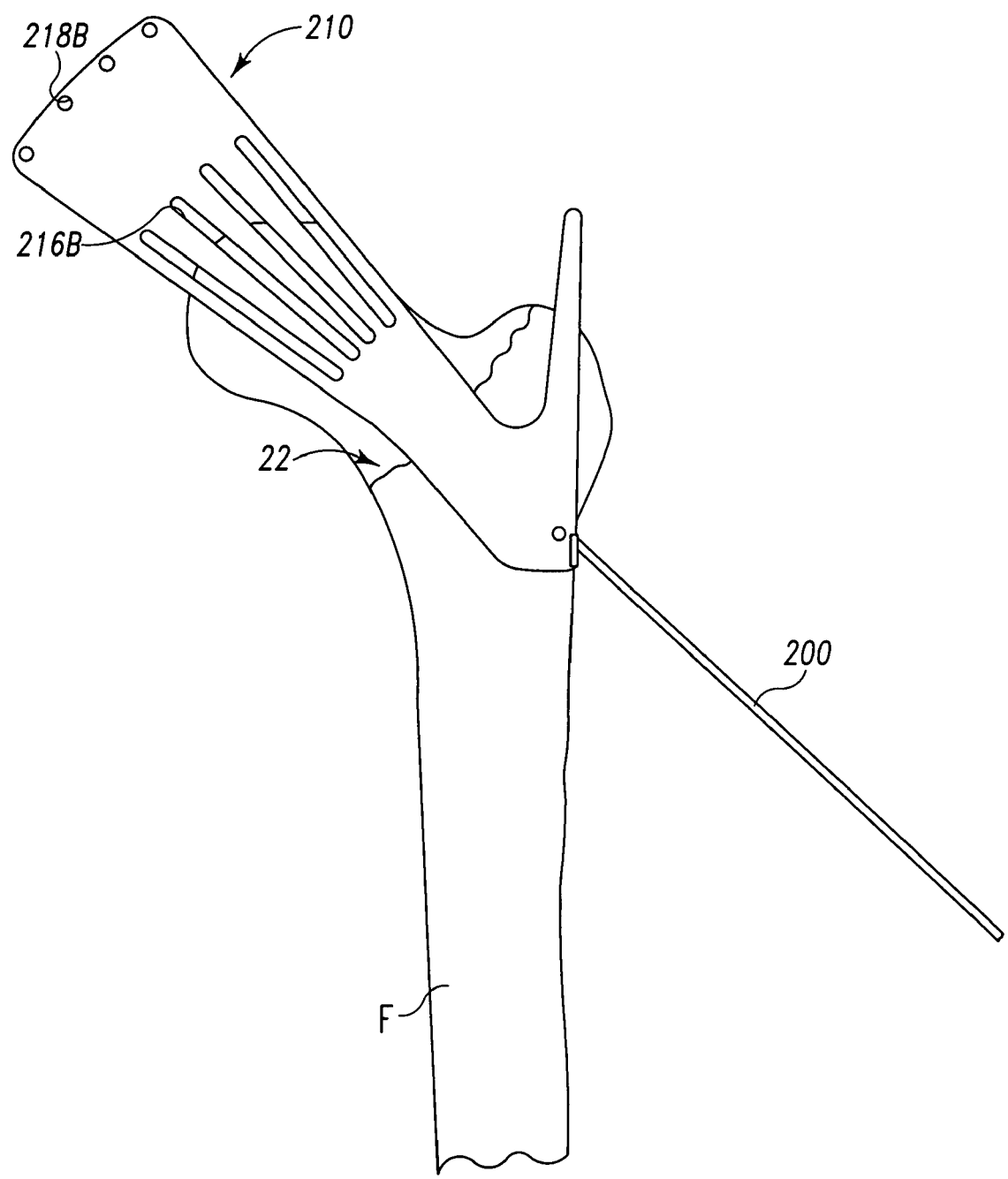
FIG. 44 is a side elevational view of the measurement apparatus of FIG. 39 being used to measure the angle of the guide wire of FIG. 37 with respect to the femur during an X-ray imaging procedure according to the present disclosure.

Alternatively, in order to measure the angle of the guide wire 200 with respect to the femur F, the measuring device 210 may be placed on the patient's skin over the femur in the manner shown in FIG. 44. Thereafter, an X-ray is taken of the femur F, the guide wire 200, and the measuring device 210. Since the measuring device 210 and the guide wire 200 are made of a radio opaque material such as stainless steel, the location of the guide wire 200 with respect to the measuring device 210 may be determined since the guide wire 200 blocks certain of the windows 216, 218 defined in the measuring device 210. In the example shown in FIG. 44, a film produced by an X-ray procedure would create an image in which the elongate window 216B and the window 218B would be blocked by the guide wire 200 thereby informing the surgeon that the angle of the guide wire 200 with respect to the femur is 130°. Thereafter, a lag screw assembly having a correspondingly angled barrel (or fastener guide) is selected by the surgeon to be implanted in the femur F.

In order to prepare the femur F for receipt of the appropriately configured lag screw assembly, a cannulated lag screw drill (not shown) is advanced over the guide wire 200 (under radiography) and into the femur F to create a fastener cavity (not shown). Upon completion of the fastener cavity, the lag screw drill is removed from the femur F, leaving the guide wire 200 in place. If necessary, a cannulated tap (not shown) may thereafter be advanced over the guide wire 200 and into the fastener cavity to create female screw threads (not shown) in the internal walls that define the fastener cavity. The lag screw assembly 4 is then advanced into the fastener cavity with the lag screw component 14 being advanced over the guide wire 200. Thereafter, the lag screw assembly 4 is secured to the femur F by rotating the lag screw 10 with a driver tool (not shown) until the lag screw assembly 4 assumes a position in relation to the femur F as shown in FIG. 4.

Once the lag screw assembly 4 has been secured within the femur as shown in FIG. 4, the bone plate 6 may be assembled to the fastener guide or barrel 12. This is accomplished with the assistance of the instrument assembly 30. In particular, using the instrument assembly 30 having the bone plate 6 attached thereto (as described above), the bone plate 6 is advanced through the incision I. After being advanced through the incision I, the bone plate 6 is advanced distally until the proximal end of the bone plate 6 is located distal to the lag screw assembly 4 as shown in FIG. 25. The bone plate 6 is then slid toward the lag screw assembly 4 so that the fastener guide 12 is passed through the access opening 29 defined in the proximal end of the bone plate 6. Also during sliding of the bone plate 6 toward the lag screw assembly 4, the projection 26 of the bone plate 6 advances into the channel 24 of the fastener guide 12. Continued advancement of the bone plate 6 in relation to the fastener guide 12 results in the seating surface SS1 of the fastener guide 12 contacting the seating surface SS2 of the bone plate 6 as shown in FIG. 26. When seating surface SS1 is in contact with the seating surface SS2, the bone plate 6 and the fastener guide 12 are in an assembled state.

During the above-described advancement of the bone plate 6 relative to the fastener guide 12, the stop structure 112 of the instrument assembly 30 is located in its upper position. When the stop structure 112 is in its upper position, the knob 116 of the actuator 114 of the instrument assembly 30 is located at its first position (shown in FIG. 26) such that the "unlocked" icon 166 is visible through the viewing opening 168 of the knob 116.

When the surgeon believes the bone plate 6 has been advanced into its assembled state with the fastener guide 12, the surgeon rotates the knob 116 clockwise so that the viewing opening 168 is moved to a second position (shown in FIG. 28) in which the viewing opening 168 is aligned with "locked" icon 164 thereby displaying the "locked" icon 164 through the viewing opening 168. If the knob 116 is prevented from moving to from its first position (shown in FIG. 26) to its second position (shown in FIG. 28), the surgeon is positively notified the bone plate 6 and the fastener guide 12 are not in an assembled state. Thus, the surgeon would need to further mate the bone plate 6 and the fastener guide 12 so that the seating surface SS1 of the fastener guide 12 is positioned in contact with the seating surface SS2 of the bone plate 6. On the other hand, if the knob 116 is allowed to move from its first position (shown in FIG. 26) to its second position (shown in FIG. 28), then a surgeon is positively notified the bone plate 6 and the fastener guide 12 are in their assembled state. When the knob 116 is positioned at its second position (shown in FIG. 28), the stop structure 112 is located at its lower position thereby retaining or locking the bone plate 6 and the fastener guide 12 in their assembled state.

If desired, prior to moving the knob 116 from its first position ("unlocked" icon displayed and red-colored groove 182 hidden from view) to its second position ("locked" icon displayed and red-colored groove 182 exposed to a user), the bone plate 6 may be impacted with an impactor 170 as shown in FIG. 17. In particular, the impactor 170 is manipulated until its distal end is received within an impactor recess 172 of the plate holder 40. Thereafter, the proximal end of the impactor 170 is tapped firmly several times (e.g. three or four) with a mallet (not shown) to transmit force to the bone plate 6 thereby ensuring the bone plate 6 and the lag screw assembly 4 are fully mated.

When the knob 116 is positioned at its second position (shown in FIG. 28), indicating that the bone plate 6 and the fastener guide 12 are in their assembled state, the guide component 60 is moved from its position shown in FIG. 17 to its position shown in FIG. 16. This is accomplished by moving the actuator 74 from its lower position (shown in solid in FIG. 8) to its upper position (shown in phantom in FIG. 8), and thereafter rotating the guide component 1800 about the axis X (see FIG. 8) from its position shown in FIG. 17 to its position shown in FIG. 16. Upon arriving at its position shown in FIG. 16, the guide component 60 becomes locked in relation to plate holder 40. At this position, the guide holes 62, 62A of the guide component 60 are respectively aligned with the fastener openings 7, 7A of the bone plate 6.

With the guide component 60 secured in its position shown in FIG. 16 (see also FIG. 8), instruments such as the drill assembly 70 may be advanced through the guide holes 62, 62A and the fastener openings 7, 7A to create fastener cavities (not shown) in the femur that are aligned with the fastener openings 7, 7A. Thereafter, the bone screws 8A, 8B (such as 4.5 mm bone screws) are driven through the fastener openings 7, 7A of the bone plate 6 and into the shaft of the femur F. The bone screws 8A, 8B are driven (one at a time) through an outer sheath S that respectively extends through the guide holes 62, 62A in the guide component. (See, e.g., FIG. 8.)

After placement of the final bone screw 8A, 8B, the driver 68 is advanced through the guide hole 62A of the guide component 60 until the drive structure 96 of the tip portion 92 of the driver mates with drive structure 100 of the coupling component 44. Thereafter, the driver 68 is rotated in the counter-clockwise direction thereby causing the coupling component 44 to be rotated in relation to the bone plate 6. Rotation of the coupling component 44 in relation to the bone plate 6 in the counter-clockwise direction causes the set of external threads 52 of the coupling component 44 to become meshingly disengaged with the set of internal threads 54 of the bone plate 6 thereby detaching (or unlocking) the plate holder 40 from the implanted bone plate 6. Thereafter, the plate holder 40 is removed from the patient P through the incision, and the incision I is closed in a conventional manner.

There is a plurality of advantages arising from the various features of each of the embodiments of the measurement apparatus described herein. It will be noted that alternative embodiments of the measurement apparatus may not include all of the features described yet still benefit from at least some of the advantages of such features. Those of ordinary skill in the art may readily devise their own implementations of the measurement apparatus that incorporates one or more of the features and fall within the spirit and scope of the present invention as defined by the appended claims.

What is claimed is:

1. A measurement apparatus comprising:
   (a) a body, wherein:
      said body includes a reference surface that defines a reference line,
      said body further defines a plane, and said reference line lies within said plane,
      said body further defines (i) a left lateral side surface located on a first side of said plane, and (ii) a right lateral side surface located on a second side of said plane opposite to said first side of said plane,
      said left lateral side surface defines a first left lateral window opening,
      said right lateral side surface defines a first right lateral window opening,
      said body further includes a first elongate window that has its length extending in a first direction,
      said first elongate window defines a first measurement line extending in said first direction,
      said first elongate window extends from said first left lateral window opening to said first right lateral window opening,
      said body further includes a first measurement indicia positioned on said left lateral side surface in association with said first elongate window,
      said first measurement line and said reference line define a first angle having a first magnitude, and
      said first measurement indicia corresponds to said first magnitude; and
   (b) a guide wire catch projecting from said body, wherein (i) said guide wire catch includes a first catch portion and a second catch portion, (ii) said first catch portion is positioned on said first side of said plane, (iii) said second catch portion is positioned on said second side of said plane, (iv) said first catch portion is configured to define a first hook, and (v) said second catch portion is configured to define a second hook; and
   (c) a guide wire, wherein (i) said first hook defines a first contact surface, (ii) said second hook defines a second contact surface, (iii) said first hook is configured to receive said guide wire therethrough when said guide wire is positioned in contact with said first contact surface, and (iv) said second hook is configured to receive said guide wire therethrough when said guide wire is positioned in contact with said second contact surface.

2. The measurement apparatus of claim 1, wherein:
   said left lateral side surface further defines a second left lateral window opening, and said right lateral side surface further defines a second right lateral window opening,
   said body further includes a second elongate window that is spaced apart from said first elongate window, said second elongate window having its length extending in a second direction,
   said second elongate window extends from said second left lateral window opening to said second right lateral window opening
   said second elongate window defines a second measurement line extending in said second direction,
   said body further includes a second measurement indicia positioned on said left lateral side surface in association with said second elongate window,
   said second measurement indicia is different from said first measurement indicia,
   said second measurement line and said reference line define a second angle having a second magnitude, and
   said second measurement indicia corresponds to said second magnitude.

3. The measurement apparatus of claim 1, wherein said body is made of a radio opaque material.

4. The measurement apparatus of claim 3, wherein said radio opaque material includes stainless steel.

5. The measurement apparatus of claim 1, wherein:
   said body includes a measurement portion and a reference portion,
   said measurement portion has said first elongate window defined therein,
   said reference portion includes said reference surface,
   a gap is defined between said measurement portion and said reference portion, and
   said reference portion includes a finger extending away from said measurement portion.

6. The measurement apparatus of claim 1, wherein:
   said first elongate window extends from said left lateral side surface to said right lateral side surface to define a transverse direction, and
   said transverse direction is substantially perpendicular to said plane.

7. The measurement apparatus of claim 1, wherein:
   said body further includes an indicia line positioned on said left lateral side surface, and
   said indicia line is aligned with said first measurement line.

8. The measurement apparatus of claim 1, wherein said first left lateral window opening is spaced apart from said first right lateral window opening.

9. A measurement apparatus comprising:
   (a) a body, wherein:
      said body includes a reference surface that defines a reference line,
      said body further defines a plane, and said reference line lies within said plane,
      said body further defines (i) a left lateral side surface located on a first side of said plane, and (ii) a right lateral side surface located on a second side of said plane opposite to said first side of said plane,
      said left lateral side surface defines a first left lateral window opening, and said right lateral side surface defines a first right lateral window opening,
      said body further includes a plurality of windows that are aligned along a first direction,
      said plurality of windows define a first measurement line extending in said first direction,
      at least one of said plurality of windows extends from said first left lateral window opening to said first right lateral window opening, said body further includes a first measurement indicia positioned on said left lateral side surface in association with said first plurality of windows, said first measurement line and said reference line define a first angle having a first magnitude, and said first measurement indicia corresponds to said first magnitude;

(b) a guide wire catch projecting from said body, wherein (i) said guide wire catch includes a first catch portion and a second catch portion, (ii) said first catch portion is positioned on said first side of said plane, (iii) said second catch portion is positioned on said second side of said plane, (iv) said first catch portion is configured to define a first hook, and (v) said second catch portion is configured to define a second hook; and (c) a guide wire, wherein: (i) said first hook defines a first contact surface, (ii) said second hook defines a second contact surface, (iii) said first hook is configured to receive said guide wire therethrough when said guide wire is positioned in contact with said first contact surface, and (iv) said second hook is configured to receive said guide wire therethrough when said guide wire is positioned in contact with said second contact surface.

10. The measurement apparatus of claim 9, wherein:

said left lateral side surface further defines a second left lateral window opening, and said right lateral side surface further defines a second right lateral window opening, said body further includes a second plurality of windows that is spaced apart from said first plurality of windows, said second plurality of windows are aligned along a second direction, at least one of said second plurality of windows extends from said second left lateral window opening to said second right lateral window opening, said second plurality of windows defines a second measurement line extending in said second direction, said body further includes a second measurement indicia positioned on said left lateral side surface in association with said second plurality of windows, said second measurement indicia is different from said first measurement indicia, said second measurement line and said reference line define a second angle having a second magnitude, and said second measurement indicia corresponds to said second magnitude.

11. The measurement apparatus of claim 9, wherein said body is made of a radio opaque material.

12. The measurement apparatus of claim 11, wherein said radio opaque material includes stainless steel.

13. The measurement apparatus of claim 9, wherein:

said body includes a measurement portion and a reference portion, said measurement portion has said at least one of said plurality of windows defined therein, said reference portion includes said reference surface, a gap is defined between said measurement portion and said reference portion, and said reference portion includes a finger extending away from said measurement portion.

14. The measurement apparatus of claim 9, wherein:

said at least one of said plurality of windows extends from said left lateral side surface to said right lateral side surface to define a transverse direction, and said transverse direction is substantially perpendicular to said plane.

15. The measurement apparatus of claim 9, wherein:

said body further includes an indicia line positioned on said left lateral side surface, and said indicia line is aligned with said first measurement line.

16. A measurement apparatus comprising:

(a) a body, wherein:

said body includes a reference surface that defines a reference line, said body further defines a plane, and said reference line lies within said plane, said body further defines (i) a left lateral side surface located on a first side of said plane, and (ii) a right lateral side surface located on a second side of said plane opposite to said first side of said plane, said left lateral side surface defines a first left lateral window opening, said right lateral side surface defines a first right lateral window opening, said body further includes a first elongate window that has its length extending in a first direction, said first elongate window defines a first measurement line extending in said first direction, said first elongate window extends from said first left lateral window opening to said first right lateral window opening, said body further includes a first measurement indicia positioned on said left lateral side surface in association with said first elongate window, said first measurement line and said reference line define a first angle having a first magnitude, and said first measurement indicia corresponds to said first magnitude; and (b) a guide wire catch projecting from said body, said guide wire catch defining a contact surface; and (c) a guide wire, wherein said contact surface of said guide wire catch is configured to contact said guide wire when said guide wire is positioned in contact with said body.

17. The measurement apparatus of claim 16, wherein:

said guide wire catch includes a hook structure that defines said contact surface, and said hook structure is configured to receive said guide wire therethrough when said guide wire is positioned in contact with said body.

18. The measurement apparatus of claim 16, wherein:

said left lateral side surface further defines a second left lateral window opening, and said right lateral side surface further defines a second right lateral window opening, said body further includes a second elongate window that is spaced apart from said first elongate window, said second elongate window having its length extending in a second direction, said second elongate window extends from said second left lateral window opening to said second right lateral window opening said second elongate window defines a second measurement line extending in said second direction, said body further includes a second measurement indicia positioned on said left lateral side surface in association with said second elongate window, said second measurement indicia is different from said first measurement indicia, said second measurement line and said reference line define a second angle having a second magnitude, and said second measurement indicia corresponds to said second magnitude.

19. The measurement apparatus of claim 16, wherein said body is made of a radio opaque material.

20. The measurement apparatus of claim 19, wherein said radio opaque material includes stainless steel.

21. The measurement apparatus of claim 16, wherein:
said body includes a measurement portion and a reference portion,
said measurement portion has said first elongate window defined therein,
said reference portion includes said reference surface,
a gap is defined between said measurement portion and said reference portion, and
said reference portion includes a finger extending away from said measurement portion.

22. The measurement apparatus of claim 16, wherein said contact surface of said guide wire catch is further configured to contact said guide wire when (i) said guide wire is positioned in contact with said body, and (ii) said guide wire extends through said guide wire catch.

* * * * *